United States Patent
Framroze

(10) Patent No.: US 10,968,207 B2
(45) Date of Patent: Apr. 6, 2021

(54) METHODS FOR PREPARING OLTIPRAZ

(71) Applicant: ST IP Holding AG, Zug (CH)

(72) Inventor: Bomi P. Framroze, Mumbai (IN)

(73) Assignee: ST IP Holding AG, Zug (CH)

( * ) Notice: Subject to any disclaimer, the term of this patent is extended or adjusted under 35 U.S.C. 154(b) by 0 days.

(21) Appl. No.: 16/854,480

(22) Filed: Apr. 21, 2020

(65) Prior Publication Data

US 2020/0247791 A1 Aug. 6, 2020

Related U.S. Application Data

(63) Continuation of application No. 16/784,915, filed on Feb. 7, 2020, which is a continuation of application No. 16/041,282, filed on Jul. 20, 2018, now abandoned, which is a continuation of application No. 14/823,256, filed on Aug. 11, 2015, now abandoned.

(30) Foreign Application Priority Data

Jun. 25, 2015 (IN) .......................... 1891/DEL/2015

(51) Int. Cl.
*C07D 409/04* (2006.01)
*C07D 241/12* (2006.01)
*C07D 241/24* (2006.01)

(52) U.S. Cl.
CPC ......... *C07D 409/04* (2013.01); *C07D 241/12* (2013.01); *C07D 241/24* (2013.01)

(58) Field of Classification Search
CPC .................................................. C07D 409/04
See application file for complete search history.

(56) References Cited

U.S. PATENT DOCUMENTS

| | | |
|---|---|---|
| 4,110,450 A | 8/1978 | Barreau et al. |
| 7,288,652 B2 | 10/2007 | Kim et al. |
| 2003/0191137 A1 | 10/2003 | Kim et al. |
| 2004/0053989 A1 | 3/2004 | Prendergast et al. |
| 2005/0163855 A1 | 7/2005 | Cho et al. |
| 2006/0106079 A1 | 5/2006 | Kim et al. |
| 2020/0172522 A1 | 6/2020 | Framroze |

OTHER PUBLICATIONS

Declaration Under 37 CFR § 1.132 of Bomi P. Framroze, Ph.D. dated Aug. 9, 2019.
Extended European Search Report for EP Application No. 16813869.1 dated Dec. 11, 2018.
International Search Report dated Dec. 27, 2016, from PCT/IN16/50197.
Second Declaration Under 37 CFR § 1.132 of Bomi P. Framroze, Ph.D. dated Apr. 17, 2020.

*Primary Examiner* — Brian E McDowell
(74) *Attorney, Agent, or Firm* — Foley Hoag LLP

(57) ABSTRACT

The invention provides improved methods of synthesizing oltipraz, which result in higher overall yield and better purity of the desired product.

9 Claims, No Drawings

METHODS FOR PREPARING OLTIPRAZ

CROSS-REFERENCE TO RELATED APPLICATIONS

This application is a continuation of U.S. patent application Ser. No. 16/784,915, filed Feb. 7, 2020, which is a continuation of U.S. patent application Ser. No. 16/041,282, filed Jul. 20, 2018, which is a continuation of U.S. patent application Ser. No. 14/823,256, filed on Aug. 11, 2015, which claims the benefit of priority to Indian provisional patent application serial number 1891/DEL/2015, filed Jun. 25, 2015; the contents of which are hereby incorporated by reference.

BACKGROUND

Oltipraz, 4-methyl-5-(pyrazin-2-yl)-3H-1,2-dithiole-3-thione, depicted in Formula I, below, was originally developed as an anti-schistosomal drug that eliminates parasitic worms. Later, it was discovered that oltipraz is a chemopreventive agent. The drug also has other known and unknown uses in the medical field.

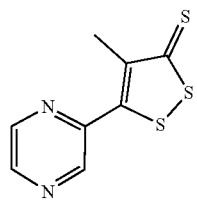

Formula I

Various syntheses of oltipraz are known in the art. However, each suffers from various disadvantages, such as low overall yield, long reaction times, risk of explosion due to the use of hydride anion, and severe environmental contamination from required large excesses of $P_2S_5$.

There exists a need for a fast, safe method of synthesizing oltipraz in high overall yield without using large excesses of $P_2S_5$.

SUMMARY

In certain embodiments, the invention relates to a method comprising the steps of:
  a) combining in a first container a first solvent and a first base;
  b) stirring the contents of the first container at a temperature of about 0° C. for about 5 minutes;
  c) adding to the first container, over a period of time of about 15 minutes, methyl propionate;
  d) stirring the contents of the first container at about 0° C. for about 15 minutes;

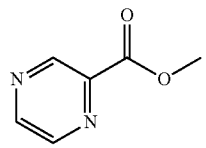

e) adding to the first container a solution of in a second solvent, wherein the solution is added over a period of time of about 30 minutes while warming the first container to a temperature of about 22° C.; and the second solvent is a mixture of tetrahydrofuran and 1,4-dioxane; and
  f) stirring the contents of the first container at about 22° C. for a first period of time.

In certain embodiments, the invention relates to any of the methods described herein, wherein the first base is sodium pentanoate or potassium t-butoxide.

In certain embodiments, the invention relates to any of the methods described herein, wherein the method is a method of synthesizing

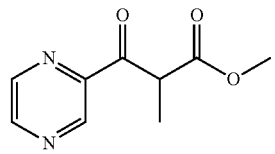

in a yield greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98%, or greater than 99%.

In certain embodiments, the invention relates to a method of synthesizing oltipraz, comprising the steps of:
  i) combining in a second container $P_2S_5$ and a first quantity of toluene;
  ii) heating the second container at a temperature of about 100° C.;
  iii) adding to the second container a solution of

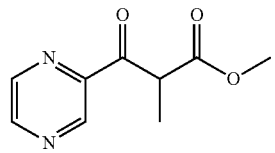

in a second quantity of toluene; and
  iv) heating the contents of the second container to reflux for a second period of time,
  wherein no xylene is added or included at any step.

In certain embodiments, the invention relates to any of the methods described herein, wherein the purity of the oltipraz produced by the claimed methods is greater than 97%, greater than 98%, or greater than 99%, as determined by gas chromatography.

In certain embodiments, the invention relates to any of the methods described herein, wherein the overall yield of oltipraz from

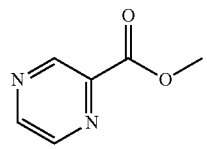

is greater than 21%, greater than 22%, greater than 23%, greater than 24%, greater than 25%, greater than 26%, greater than 27%, greater than 28%, greater than 29%, or greater than 30%.

In certain embodiments, the invention relates to any of the methods described herein, wherein the overall yield of oltipraz from

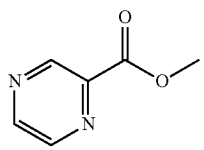

is greater than 21%, and the purity of the resulting oltipraz is greater than 97%, as determined by gas chromatography.

DETAILED DESCRIPTION

I. Overview

In certain embodiments, the invention relates to an improved method of synthesizing oltipraz. In certain embodiments, the method involves Step 2 or Step 3 (or both Step 2 and Step 3 in succession) as depicted in Scheme 1.

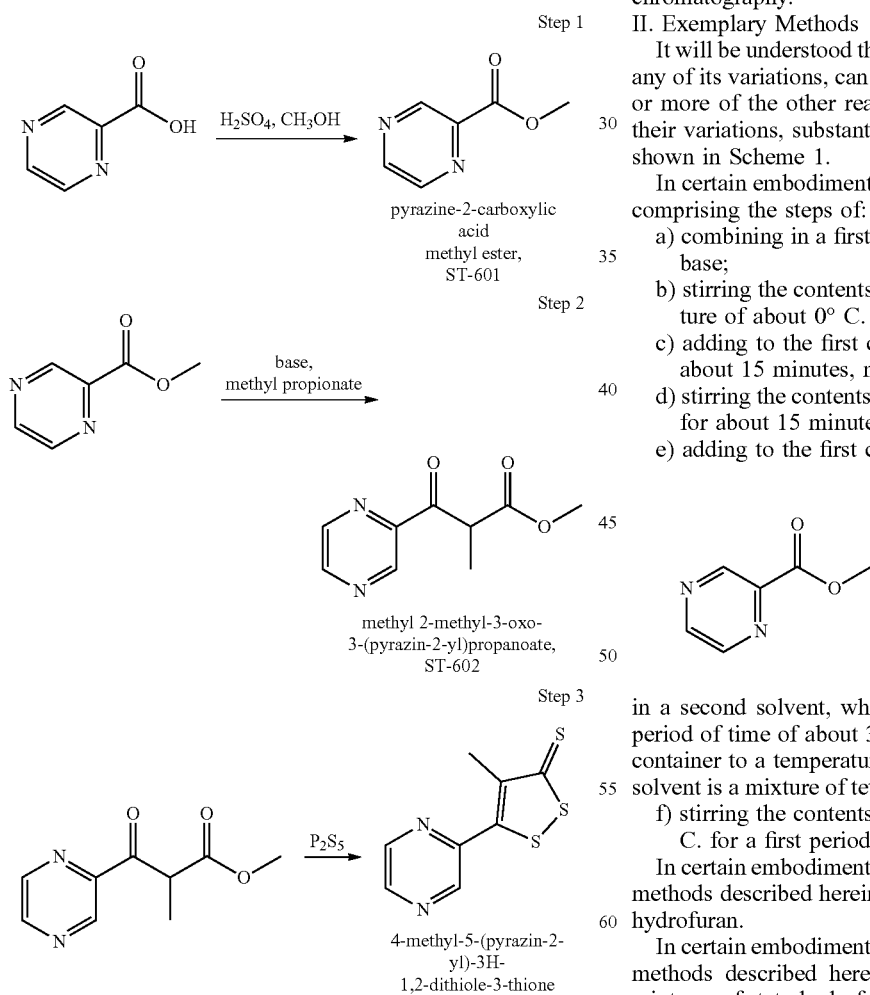

In certain embodiments, the invention relates to any one of the methods described herein, wherein Step 2 does not involve sodium hydride.

In certain embodiments, the invention relates to any one of the methods described herein, wherein the yield of Step 2 is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98%, or greater than 99%.

In certain embodiments, the invention relates to any one of the methods described herein, wherein the overall yield of Step 2 and Step 3 is greater than 21%, greater than 22%, greater than 23%, greater than 24%, greater than 25%, greater than 26%, greater than 27%, greater than 28%, greater than 29%, or greater than 30%.

In certain embodiments, the invention relates to any one of the methods described herein, wherein the purity of the oltipraz produced by the claimed methods is greater than 97%, greater than 98%, or greater than 99%, as determined by gas chromatography.

In certain embodiments, the invention relates to any one of the methods described herein, wherein the overall yield of Step 2 and Step 3 is greater than 21%, and the purity of the resulting oltipraz is greater than 97%, as determined by gas chromatography.

II. Exemplary Methods

It will be understood that any reaction described herein, in any of its variations, can be combined in sequence with one or more of the other reactions described herein, in any of their variations, substantially in analogy with the sequence shown in Scheme 1.

In certain embodiments, the invention relates to a method comprising the steps of:
   a) combining in a first container a first solvent and a first base;
   b) stirring the contents of the first container at a temperature of about 0° C. for about 5 minutes;
   c) adding to the first container, over a period of time of about 15 minutes, methyl propionate;
   d) stirring the contents of the first container at about 0° C. for about 15 minutes;
   e) adding to the first container a solution of

[structure]

in a second solvent, wherein the solution is added over a period of time of about 30 minutes while warming the first container to a temperature of about 22° C.; and the second solvent is a mixture of tetrahydrofuran and 1,4-dioxane; and
   f) stirring the contents of the first container at about 22° C. for a first period of time.

In certain embodiments, the invention relates to any of the methods described herein, wherein the first solvent is tetrahydrofuran.

In certain embodiments, the invention relates to any of the methods described herein, wherein the first solvent is a mixture of tetrahydrofuran and 1,4-dioxane. In certain embodiments, the invention relates to any of the methods described herein, wherein the first solvent is about a 5:1, about a 4:1, or about a 3:1 mixture by volume of tetrahydrofuran and 1,4-dioxane. In certain embodiments, the invention relates to any of the methods described herein, wherein the first solvent is about a 4:1 mixture by volume of tetrahydrofuran and 1,4-dioxane.

In certain embodiments, the invention relates to any of the methods described herein, wherein the first base is sodium pentanoate or potassium t-butoxide.

In certain embodiments, the invention relates to any of the methods described herein, wherein the concentration of the first base in the first solvent is from about 1.0 M to about 1.8 M. In certain embodiments, the invention relates to any of the methods described herein, wherein the concentration of the first base in the first solvent is about 1.0 M, about 1.2 M, about 1.4 M, about 1.6 M, or about 1.8 M. In certain embodiments, the invention relates to any of the methods described herein, wherein the concentration of the first base in the first solvent is about 1.4 M.

In certain embodiments, the invention relates to any of the methods described herein, wherein the mole ratio of first base to methyl propionate is from about 3:1 to about 1:1. In certain embodiments, the invention relates to any of the methods described herein, wherein the mole ratio of first base to methyl propionate is about 3:1, about 2:1, or about 1:1. In certain embodiments, the invention relates to any of the methods described herein, wherein the mole ratio of first base to methyl propionate is about 1:1.

In certain embodiments, the invention relates to any of the methods described herein, wherein the concentration of

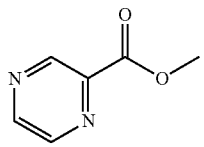

in the second solvent is from about 1.6 M to about 2.0 M. In certain embodiments, the invention relates to any of the methods described herein, wherein the concentration of

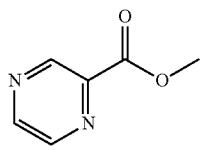

in the second solvent is about 1.6 M, about 1.8 M, or about 2.0 M. In certain embodiments, the invention relates to any of the methods described herein, wherein the concentration of

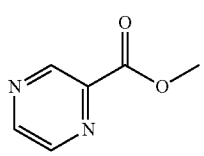

in the second solvent is about 1.8 M.

In certain embodiments, the invention relates to any of the methods described herein, wherein the mole ratio of methyl propionate to

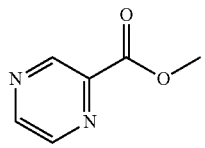

is from about 2:1 to about 1.6:1. In certain embodiments, the invention relates to any of the methods described herein, wherein the mole ratio of methyl propionate to

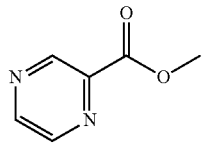

is about 2:1, about 1.8:1, or about 1.6:1. In certain embodiments, the invention relates to any of the methods described herein, wherein the mole ratio of methyl propionate to

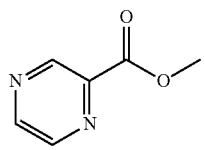

is about 1.8:1.

In certain embodiments, the invention relates to any of the methods described herein, wherein the second solvent is from about a 1.2:1 to about a 0.8:1 mixture by volume of tetrahydrofuran and 1,4-dioxane. In certain embodiments, the invention relates to any of the methods described herein, wherein the second solvent is about a 1.2:1, about a 1:1, or about a 0.8:1 mixture by volume of tetrahydrofuran and 1,4-dioxane. In certain embodiments, the invention relates to any of the methods described herein, wherein the second solvent is about a 1:1 mixture by volume of tetrahydrofuran and 1,4-dioxane.

In certain embodiments, the invention relates to any of the methods described herein, wherein the first period of time is from about 2 h to about 10 h. In certain embodiments, the invention relates to any of the methods described herein, wherein the first period of time is about 2 h, about 3 h, about 4 h, about 5 h, about 6 h, about 7 h, about 8 h, about 9 h, or about 10 h. In certain embodiments, the invention relates to any of the methods described herein, wherein the first period of time is about 6 h.

In certain embodiments, the invention relates to any of the methods described herein, wherein the method is a method of synthesizing

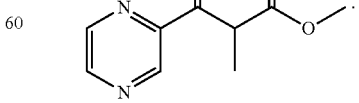

In certain embodiments, the invention relates to any of the methods described herein, wherein the method is a method of synthesizing

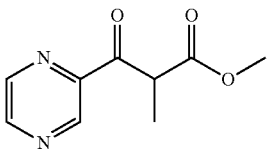

in a yield greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98%, or greater than 99%.

In certain embodiments, the invention relates to any of the methods described herein, wherein the method is a method of synthesizing

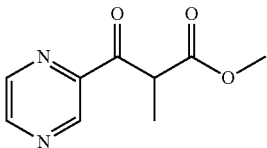

in a yield greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98%, or greater than 99% without purification other than isolation.

In certain embodiments, the invention relates to any of the methods described herein, wherein the method consists essentially of steps (a)-(f).

In certain embodiments, the invention relates to a method comprising the steps of:
  i) combining in a second container $P_2S_5$ and a first quantity of toluene;
  ii) heating the second container at a temperature of about 100° C.;
  iii) adding to the second container a solution of

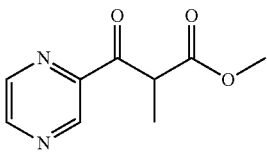

in a second quantity of toluene; and
  iv) heating the contents of the second container to reflux for a second period of time, wherein no xylene is added or included at any step.

In certain embodiments, the invention relates to a method comprising the steps of:
  i) combining in a second container $P_2S_5$, a first quantity of toluene, a first quantity of water, and a phase transfer catalyst;
  ii) heating the second container at a temperature of about 100° C.;
  iii) adding to the second container a solution of

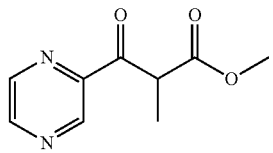

in a second quantity of toluene; and
  iv) heating the contents of the second container to reflux for a second period of time,
wherein no xylene is added or included at any step.

In certain embodiments, the invention relates to any of the methods described herein, wherein the concentration of $P_2S_5$ in the first quantity of toluene is from about 0.2 M to about 0.5 M. In certain embodiments, the invention relates to any of the methods described herein, wherein the concentration of $P_2S_5$ in the first quantity of toluene is about 0.2 M, about 0.25 M, about 0.3 M, about 0.35 M, about 0.4 M, about 0.45 M, or about 0.5 M.

In certain embodiments, the invention relates to any of the methods described herein, wherein $P_2S_5$ and the first quantity of toluene are combined in the second container under an inert atmosphere. In certain embodiments, the invention relates to any of the methods described herein, wherein $P_2S_5$ and the first quantity of toluene are combined in the second container under a nitrogen atmosphere.

In certain embodiments, the invention relates to any of the methods described herein, wherein the volume ratio of the first quantity of toluene to the first quantity of water is about 12:1, about 10:1, or about 8:1. In certain embodiments, the invention relates to any of the methods described herein, wherein the volume ratio of the first quantity of toluene to the first quantity of water is about 10:1.

In certain embodiments, the invention relates to any of the methods described herein, wherein the phase transfer catalyst is a tetraalkylammonium salt or a tetraalkylphosphonium salt. In certain embodiments, the invention relates to any of the methods described herein, wherein the phase transfer catalyst is a tetrabutylphosphonium salt. In certain embodiments, the invention relates to any of the methods described herein, wherein the phase transfer catalyst is tetrabutylphosphonium halide. In certain embodiments, the invention relates to any of the methods described herein, wherein the phase transfer catalyst is tetrabutylphosphonium chloride.

In certain embodiments, the invention relates to any of the methods described herein, wherein the concentration of

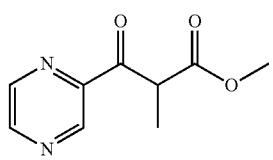

in the second quantity of toluene is from about 0.2 M to about 0.4 M. In certain embodiments, the invention relates to any of the methods described herein, wherein the concentration of

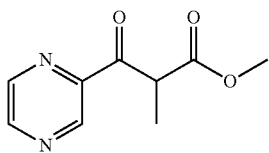

in the second quantity of toluene is about 0.2 M, about 0.3 M, or about 0.4 M.

In certain embodiments, the invention relates to any of the methods described herein, wherein the mole ratio of $P_2S_5$ to

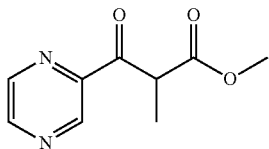

is from about 1.2:1 to about 0.6:1. In certain embodiments, the invention relates to any of the methods described herein, wherein the mole ratio of $P_2S_5$ to

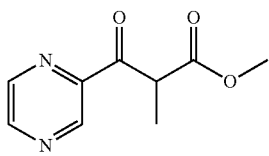

is about 1.2:1, about 1.1:1, about 1:1, about 0.9:1, about 0.8:1, about 0.7:1, or about 0.6:1.

In certain embodiments, the invention relates to any of the methods described herein, wherein the second period of time is from about 2 h to about 10 h. In certain embodiments, the invention relates to any of the methods described herein, wherein the second period of time is about 2 h, about 3 h, about 4 h, about 5 h, about 6 h, about 7 h, about 8 h, about 9 h, or about 10 h. In certain embodiments, the invention relates to any of the methods described herein, wherein the second period of time is about 6 h.

In certain embodiments, the invention relates to any of the methods described herein, wherein the

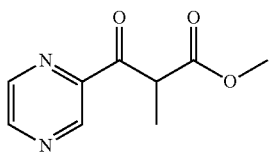

is synthesized according to steps (a)-(f), described above.

In certain embodiments, the invention relates to any of the methods described herein, wherein the mole ratio of

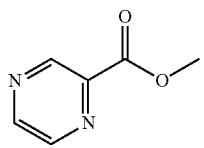

to $P_2S_5$ is from about 0.8:1 to about 1.8:1. In certain embodiments, the invention relates to any of the methods described herein, wherein the mole ratio of

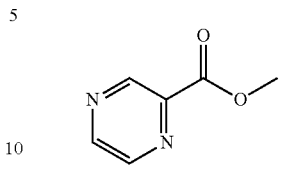

to $P_2S_5$ is about 0.8:1, about 0.9:1, about 1:1, about 1.1:1, about 1.2:1, about 1.3:1, about 1.4:1, about 1.5:1, about 1.6:1, about 1.7:1, or about 1.8:1. In certain embodiments, the invention relates to any of the methods described herein, wherein the mole ratio of

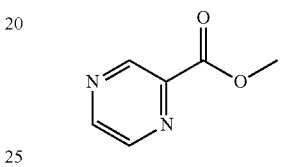

to $P_2S_5$ is about 0.9:1. In certain embodiments, the invention relates to any of the methods described herein, wherein the mole ratio of

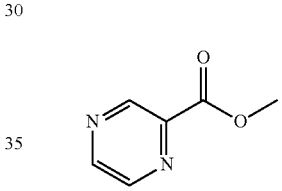

to $P_2S_5$ is about 1.4:1.

In certain embodiments, the invention relates to any of the methods described herein, wherein the method is a method of synthesizing oltipraz.

In certain embodiments, the invention relates to any of the methods described herein, wherein the overall yield of oltipraz from

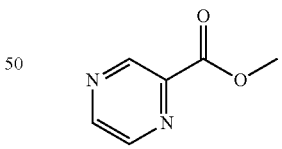

is greater than 21%, greater than 22%, greater than 23%, greater than 24%, greater than 25%, greater than 26%, greater than 27%, greater than 28%, greater than 29%, or greater than 30%.

In certain embodiments, the invention relates to any of the methods described herein, wherein the purity of the oltipraz produced by the claimed methods is greater than 97%, greater than 98%, or greater than 99%, as determined by gas chromatography.

In certain embodiments, the invention relates to any of the methods described herein, wherein the overall yield of oltipraz from

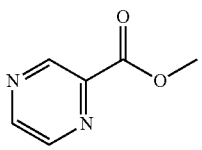

is greater than 21%, and the purity of the resulting oltipraz is greater than 97%, as determined by gas chromatography.

In certain embodiments, the invention relates to any of the methods described herein, wherein the method consists essentially of steps (i)-(iv).

In certain embodiments, the invention relates to any of the methods described herein, wherein the method consists essentially of steps (a)-(f) and steps (i)-(iv).

In certain embodiments, the invention relates to any one of the methods described herein, further comprising the steps outlined in any other method described herein.

In certain embodiments, the invention relates to the use of any one of the compounds described herein in the manufacture of a medicament.

Definitions of variables in the structures in the schemes herein are commensurate with those of corresponding positions in the formulae delineated herein.

In certain embodiments, the compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. Optical isomers may be prepared, for example, by resolving a racemic mixture. The resolution can be carried out in the presence of a resolving agent, by chromatography or by repeated crystallization or by some combination of these techniques which are known to those skilled in the art. Further details regarding resolutions can be found in Jacques, et al., Enantiomers. Racemates, and Resolutions (John Wiley & Sons, 1981).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991): L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

EXEMPLIFICATION

The present invention is further illustrated by the following Example which should not be construed as limiting in any way. The Examples and discoveries described herein are representative. As such, the studies and results described in the Examples section herein may be used as a guideline.

Example 1—Synthesis of Pyrazine-2-Carboxylic Acid Methyl Ester, ST-601 (Step 1)

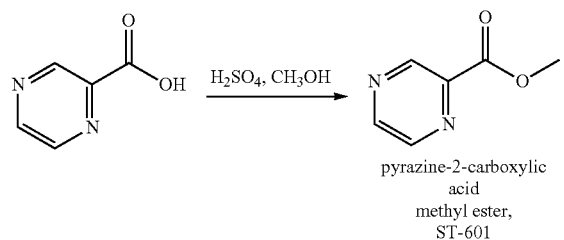

pyrazine-2-carboxylic acid methyl ester, ST-601

Input:
Pyrazinoic acid (OT-1) (1758 g, SM)
Sulfuric Acid (69.5 g)
MeOH (8.8 L)
Procedure:
  Charged MeOH (8.8 L) and OT-1 (1758 g) at RT.
  Charged $H_2SO_4$ (69.5 g) in one portion (21-22° C. exotherm). Heated to (60-65° C.) and stirred at 55-65° C. for 19 hours.
19 h, 96.0% OT-2 and 4.0% OT-1 by HPLC
  Reaction was cooled to 15/30° C. No precipitate formed.
  $NaHCO_3$ (180 g) was charged in lots. The solution bubbled slightly and quickly went from yellow to pink. The mixture was stirred for 5 min at 15/30° C.
  The mixture was then concentrated to 1.5-2.5 vol at ≤30° C.
  Charged NaCl (0.700 g) in water (2.5 vol). Upon stirring, solution became clear.
  Stirred for 15 min at 15/30° C. After stirring, the aqueous layer became slightly cloudy. The solids were filtered off and the layers were separated.
  The aqueous layer was extracted with DCM (3×2 vol.). TLC indicated that extraction was complete after 3rd extraction.
  Organic layers were dried over anhydrous $Na_2SO_4$ (0.4 g/g SM).
  Concentrated to 1.5-2.5 vol under vacuum at ≤30° C. Some precipitate formed.
  Charged heptanes (8 vol) over a minimum of 30 min. Pale white slurry. Let stir overnight.
  Stirred at −5/−15° C. for a minimum of 1 hr. Solids were filtered off and rinsed with cold heptanes
  (2×1 vol.) Pulled solids dry on filter for 10 min. Dried in vacuum oven at ≤30° C. to constant mass. Dried over weekend. Solids went from pale white to light brown.
  Color changed, but no degradation was observed.

Output material: ST-601
Lot No.: 2463-24-1
Appearance: light Brown Solids
Yield: 1721 g (91.0%)
HPLC purity: 98.9%
$^1$H NMR—Conforms to structure Example 2—Synthesis of methyl 2-methyl-3-oxo-3-(pyrazin-2-yl)propanoate, ST-602 (Step 2)

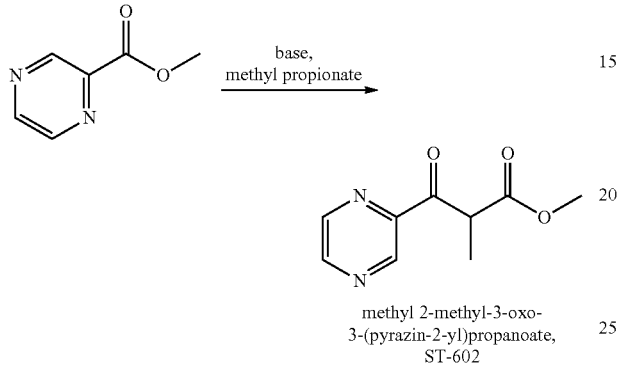

methyl 2-methyl-3-oxo-3-(pyrazin-2-yl)propanoate, ST-602

Input:
ST-601 (1000 g); Lot #2463-24-1
Methyl propionate (64 g+893 g); Lot #11-2713-56+11-2713-57+R11-1913-101
NaH in mineral oil, 60 wt. %, (579 g)
Toluene (10 vol)
Procedure:
  Charged ST-601 (1 kg), NaH, 60 wt. % (579 g) and toluene (10 vol) and stirred at 15/25° C. No reaction (no gas evolution, exotherm or appearance change).
  Charged methyl propionate (64 g). No immediate reaction (no gas evolution, exotherm or appearance change) at 15/25° C.
  Charged MeOH (85 g) at 15/25° C. Immediately started to react (gas evolution, exotherm). Heated to 30/40° C.
  Charged methyl propionate (893 g) at 30/40° C. over 5 h. The reaction was slower in the beginning, but became faster (more exotherm and gas evolution) after 1-2 h when ~0.3 eq of methyl propionate was charged. Stirred at 30/40° C. for 88 h.
64 h, 30/35° C., brown slurry, practically no gas evolution observed, IPC HPLC1: 74.4%+14.1%=88.5% of ST-602 at 4.81 min and 5.62 min; 1.2% of ST-601 at 1.97 min; 5.8% of "Int" at 3.21 min.
72 h, 35° C., IPC HPLC2: 47.8%+42.9%=90.7% of ST-602; 0.9% of ST-601; 4.3% of "Int" 88 h, 38° C., IPC HPLC3: 60.3%+32.6%=92.9% of ST-602; 0.64% of ST-601; 1.8% of "Int"
Reaction was cooled to 15/20° C.
Charged AcOH (2.5 eq) over a minimum of 1 hr. Exothermic. Slightly thick, brown suspension.
Charged 10% NaCl solution (8 vol) over a minimum of 1 h at 15/30° C. Slight exotherm. Brown, biphasic solution. Let stir at 15/30° C. for a minimum of 30 min to dissolve all solids.
The phases were separated. Both the aqueous and the organic phases were brown.
The organic phase was washed with a 10% NaCl solution (5 vol).
The organic phase was washed with NaHCO$_3$ (0.1 g/g SM) in 10% aq. NaCl solution (5 vol.)
The organic phase was dried over anhydrous sodium sulfate (0.2 g/g SM) for a minimum of 2 hrs.
Solids were filtered off and rinsed with Toluene (1×1 vol)
Concentrated to 3-4 vol at ≤50° C.
Isolated material: ST-602
Lot No.: 2463-52-2
Appearance: light brown liquid
Yield: Assumed 100% (1406 g net directly used in next step)
HPLC: 94.3% of ST-602

Example 3—Synthesis of crude 4-methyl-5-(pyrazin-2-yl)-3H-1,2-dithiole-3-thione, ST-617 (Step 3)

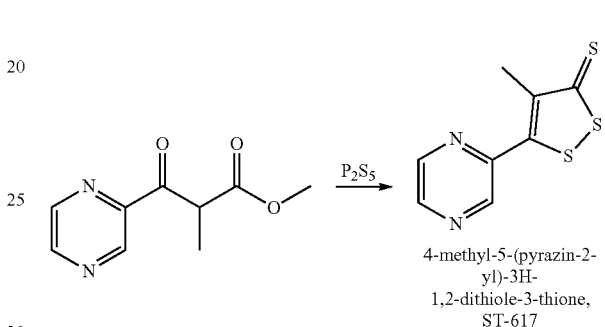

4-methyl-5-(pyrazin-2-yl)-3H-1,2-dithiole-3-thione, ST-617

Input:
ST-602 (from 1 kg of ST-601 (SM), 1 eq); Lot #2463-52-2
P$_2$S$_5$ (1931 g); Lot #11-1513-52
Toluene (15 vol)
Observations:
  Charged ST-602 in toluene (~3.5 L; 3-4 vol) to P$_2$S$_5$ (1931 g) in toluene (10 L; 10 vol). Rinsed with toluene (1 L; 1 vol). No exothermic effect, yellow slurry.
  Reaction over after 36 h at 95-97° C.
36 h, ~95° C., IPC HPLC lot #2463-54-1: 95.2% of ST-617 at 6.85 min and 4.8% of ST-602 at 4.79 min
Work-up (after 36 h at ~95° C.): Cooled to RT over 20 mins
Charged the slurry via a transfer line to a mixture of Na$_2$CO$_3$ (2686 g; 3.5 eq), water (15 L; 15 vol) and THF (5 L; 5 vol) at 15/30° C. over a minimum of 1 h—weak exothermic effect and no gas evolution observed.
The resulting mixture was slowly transferred back to the parent flask—some gas evolution observed. Minor insolubles were observed.
The resulting mixture was stirred at RT for 65 h (shouldn't need more than 12 h) to complete gas evolution/quench of the reaction mixture
The resulting mixture was passed through a 0.5" celite bed to remove fine insolubles.
The organic layer was separated, dried with Na$_2$SO$_4$ (200 g; 0.2 g/g SM) and concentrated under reduced pressure at ≤50° C. to 2-4 L (2-4 vol) residue volume (3 L actual)—product precipitates during concentration.
The resulting slurry was diluted with MeOH (1.5 L; 1.5 vol) and stirred at RT for 2 h.
The solids were collected by filtration, rinsed with MeOH (2×500 mL; 2×0.5 vol) followed by heptane (1 L+0.5 L; 1+0.5 vol).
Dried in air to yield constant weight.

Isolated material: ST-603 (crude ST-617)
Lot No.: 2463-55-1
Appearance: red solid powder (crystals not uniform)
Yield: 223 g (14%)
HPLC: 99% by R&D method Example 4—Purification of Crude ST-617 (Step 4)

Input:
ST-603 (220 g); Lot #2463-55-1
DMSO (2.2 L+220 mL)
Water (330 mL; 1.5 vol)
Observations:
  Added ST-603 into DMSO (2.2 L) and heated to 65° C.
  Clear solution in DMSO at ~65° C. Heated further to ~80° C. and hot filtered at ~80° C.
  Hot filtration was easy to perform (no fast precipitation of product).
  Diluted with water at 70/85° C. to initiate product precipitation.
  The mixture was chilled/stirred at RT for 1 hour
  Collected the solids by filtration, rinsed with 5:1 DMSO/water (2×1.5 vol) and MeOH (2×1.5 vol) sequentially.
  Re-slurried in MeOH (8 mL) at RT for 70 h (shouldn't need more than 4-6 hours) to help wash out DMSO and collected by filtration.
  Finally rinsed with MeOH (2×1.5 vol) and dried in a vacuum oven at 30/40° C. to yield constant weight.
Isolated material: ST-617
Lot No.: 2463-57-1
Appearance: brown-red solid
Yield: 191 g (87%)
HPLC: 99.5% by R&D method
$^1$H NMR (CDCl$_3$): conforms to structure (clean) with residual DMSO (0.3 wt. %)

Example 5—Synthesis of Pyrazine-2-Carboxylic Acid Methyl Ester, ST-601 (Step 1)

Aim: Carry Out 170-g-Scale Step 1
Procedure:
1. Added 900 mL of MeOH and 175 g of OT-1 into a 2-neck 2-liter RBF at 22° C. on a heating mantle.
2. Added 7 grams of concentrated sulfuric acid in one portion into the RBF.
3. Heated to 65° C. and stirred for 24 hours.
4. TLC at 24 hrs indicates little to no OT-1 (Rf 0.1 in 95:5 Hexane:EtOAc) left and new spot which is the same as authentic ST-601 at Rf 0.7
5. Reaction was cooled to RT (22° C.). No precipitate formed.
6. 75 g of Sodium Bicarbonate was added. Slight gas evolution and colour goes from yellow to pink.
7. The mixture was stirred for 10 min at 22° C.
8. The mixture was transferred to a 1-neck RBF and set on a rotovap.
9. The mixture was then concentrated to ~200 mL at ≤30° C. Added a prepared solution of 70 g of NaCl in 400 mL of water. Upon stirring, the solution became clear. Stirred for 10 min at 22° C. After stirring, the solution became slightly cloudy. The solids were filtered on a Buchner filter.
12. The aqueous layer was extracted three times with 200 ml of dichloromethane each time
13. The dichloromethane layers were combined and 50 g of anhydrous sodium sulfate was added to the solution. Stirred for 5 min and filtered on Buchner.
14. The solution was concentrated to ~50 mL on a Rotovap under vacuum at ≤30° C. Some precipitate was visible but very fine.
15. Added 700 mL of mixed heptanes over ~45 min. A pale white slurry formed which was stirred gently overnight.
16. Cooled the RBF to −15° C. (dry ice batch) and stirred for 2 hours.
17. Thicker solids formed which were filtered on a Buchner.
18. The residue was rinsed with refrigerated mixed heptanes two times with 200 mL each.
19. Pulled the solids dry on the Buchner for 15 min. Transferred to tared dish.
20. Set to dry in vacuum oven at ≤30° C. overnight.
21. Color of powder is pale brown.
22. GC (in lab) shows 98.4% purity versus authentic
23. Weight of powder is 168 g (89% yield)
24. Labelled as ST-601-001

Example 6—Synthesis of methyl 2-methyl-3-oxo-3-(pyrazin-2-yl)propanoate, ST-602 (Step 2)

Aim: Establish Baseline for Step 2 using NaH as the Base.
Procedure
1. Add 2.5 g (0.0181 mole) of ST-601, 1.4 g of 60% NaH in oil and 25 mL of toluene into a 100-mL 2-neck RBF at 22° C. and stir for 30 min to thoroughly strip the oil off the NaH. No gas evolution or temperature change was observed.
2. Added 250 mg of methyl propionate into the flask with no exotherm or gas evolution observed.
3. Added 2.5 mL of methanol.
4. Immediately started to react with gas evolution and exotherm.
5. Heated to 40° C.
6. Added 2.3 g of methyl propionate dropwise from addition funnel at 1 mL/20 min.
7. The reaction became more vigorous after 30 min of addition.
8. Stirred at 40° C.
9. Monitored by HPLC (GeoChem Method ST1). After 24 hrs at 40° C. the reaction is a brown slurry and no gas was being evolved. HPLC showed two peaks (same as for authentic ST-602) totaling 82.4% and 2.1% of ST-601 and with an intermediate peak of 15.2% (all area % peaks)
10. After 72 h at 40° C. the reaction is a brown slurry with no gas being evolved. HPLC showed two peaks (same as for authentic ST-602) totaling 96.0% and 0.5% of ST-601 with an intermediate peak of 1% (all area % peaks)
11. The reaction was cooled to 22° C. (RT) and 3 mL of glacial acetic acid was added slowly. (some slow gas evolution). Then added in 100 mL of 10% aq. NaCl solution with stirring. The organic layer was separated and washed with 100 mL of 10% aq. NaCl+10% NaHCO$_3$ and dried over 10 g of sodium sulfate anhydrous. The slurry was filtered on a Buchner and the reside washed 1× with 20 mL of toluene.
12. Concentrated on a rotovap at ≤50° C. to ~5 mL.
13. The above reference standard reaction product will be considered the crude standard required for use of un-isolated ST-602 in the next cyclization step.
14. The orange-brown solution will be used as is in Step 3 cyclization yield verification step.
15. Labeled as ST-602-002

Example 7—Alternative synthesis of methyl 2-methyl-3-oxo-3-(pyrazin-2-yl)propanoate, ST-602 (Step 2)

Aim: Replace Base in Step 2 with t-butoxide
Procedure
1. Added 4.1 g (0.0362 mole) of potassium t-butoxide powder and 25 mL of dry THF into a 100-mL 2-neck RBF at 0° C. Stirred for 5 minutes
2. Added 2.9 g (0.0326 mole) of methyl propionate (Mwt 88) into the flask using a dropping funnel over 15 minutes. Color turns yellow.
3. Stirred for an additional 15 minutes at 0° C.
4. 2.5 g (0.0181 mole) of ST-601 was dissolved in 10 mL of THF and added into the reaction over 30 minutes while allowing the reaction to come to RT(~½ hr). No gas evolution or exotherm.
5. Stirred at reflux for 24 hours
6. Monitored by HPLC (Method ST1). After 24 hrs at reflux the reaction is a brown slurry HPLC showed two peaks (same as for authentic ST-602) totaling 32.6% and 39.7% of ST-601 and with an intermediate peak of 18% (all area % peaks)
8. After 72 hrs at reflux the reaction was a dark brown slurry.
9. HPLC showed two peaks (same as for authentic ST-602) totaling 36.8% and 38.2% of ST-601 with an intermediate peak of 12.5% (all area % peaks)
10. Concentrated on a rotovap at ~50° C.
11. The 2.5 dark brown solution will be used as is in Step 3 cyclization yield verification step.
12. Labeled as ST-602-003

Example 8—Alternative synthesis of methyl 2-methyl-3-oxo-3-(pyrazin-2-yl)propanoate, ST-602 (Step 2)

Aim: Replace base in Step 2 with sodium pentanoate
Procedure
1. Add 4.5 g (0.0362 mole) of sodium pentanoate (Mwt 124) powder and 25 mL of dry THF into a 100-mL 2-neck RBF at 0° C. Stirred for 5 minutes
2. Added 2.9 g (0.0326 mole) of methyl propionate (Mwt 88) into the flask using a dropping funnel over 15 minutes. Color turned yellow.
3. Stirred for an additional 15 minutes at 0° C.
4. Add 2.5 g (0.0181 mole) of ST-601 was dissolved in 10 mL of THF and added into the reaction over 30 minutes while allowing the reaction to come to RT (~½ hr). No gas evolution or exotherm.
5. Stirred at reflux for 24 hours
6. Monitored by HPLC (Method ST1). After 24 hrs at reflux the reaction is a yellow-brown slurry
7 HPLC showed two peaks (same as for authentic ST-602) totaling 18.3% and 20.4% of ST-601 and with an intermediate peak of 39.9% (all area % peaks)
8. After 72 hrs at reflux the reaction is a dark brown slurry.
10. HPLC showed two peaks (same as for authentic ST-602) totaling 26.9% and 21.7% of ST-601 with an intermediate peak of 35.3% (all area % peaks)
11. Concentrated on a rotovap at ≤50° C. to ~5 mL
12. The dark brown solution will be used as is in Step 3 cyclization yield verification step.
13. Labeled as ST-602-004

Example 9—Synthesis of crude 4-methyl-5-(pyrazin-2-yl)-3H-1,2-dithiole-3-thione, ST-617 (Step 3)

Aim: Establish baseline for Step 3
Procedure
1. Added 5.65 g (0.025 mole) of $P_2S_5$ and 50 mL of Toluene into a 100-mL 2-neck RBF under nitrogen
2. Yellow slurry but easily stirable.
3. Added crude ST-602-002 solution (~5 mL). Yellow-brown slurry.
4. Started stirring and heated to 50° C., color changed to reddish brown in 10 min. Slow $H_2S$ gas evolution was observed which is passed through a caustic bubbler and no $H_2S$ was exited.
5. Continued heating up to 95° C. and let stir for 36 hours.
6. A sample was taken for HPLC (method ST-1). No starting material present. Product ST-603 was present but also many other small peaks. Area % of ST-603 is 88.8% against authentic sample with 5.4% ST-602
7. The reaction was cooled to 22° C. (RT)
8. In a 100-mL beaker was prepared a quenching mixture of 7 g of solid $Na_2CO_3$ dissolved in 30 mL water and 10 mL of THF at RT.
9. To the above beaker was slowly added (over 10 min) the content of the reaction flask. Weak exotherm was observed but no $H_2S$ gas was smelt at all.
10. The resulting mixture was stirred over 12 hours to complete quench of the reaction (in a very high vent hood attached to a scrubber for safety). Some insolubles were visible at the end of the 12 hours.
11. The reaction slurry was passed through a 1"-celite bed to remove fine insolubles.
12. The organic layer was separated (both are colored red), dried over 2 g anhydrous sodium sulfate, and concentrated on a rotovap at ≤50° C. to 20 mL volume. Solid ppt is observed during concentration.
13. The resulting slurry was diluted with 20 mL of methanol and stirred at RT for 2 h.
14. The solids were collected by filtration, rinsed 2× with 20 mL of refrigerated cold methanol followed by 20 mL of cold heptane.
15. Dried in vacuum oven to constant weight.
16. Weight of powder is 348 mg (~12% yield)
17. HPLC showed 98.2% product against authentic sample.
18. Sent 20 mg to IPAC for $^1H$ NMR.
19. Labelled as ST-603-005

Example 10—Synthesis of crude 4-methyl-5-(pyrazin-2-yl)-3H-1,2-dithiole-3-thione, ST-617 (Step 3)

Aim: Carry out Step 3 to study cyclization of crude mixture from potassium t-butoxide Condensation.
Procedure
1. Added 5.65 g (0.025 mole) of $P_2S_5$ and 50 mL of Toluene into a 100-mL 2-neck RBF under nitrogen.
2. Yellow slurry.
3. Added crude ST-602-003 solution (~5 mL). Brown slurry (difficult to stir)
4. Started stirring and heated to 50° C. No color change. Slow $H_2S$ gas evolution is observed which is passed through a caustic bubbler and no $H_2S$ is exited.
5. Continued heating up to 95° C. and let stir for 36 hours.
6. A sample was taken for HPLC (method ST-1): 601 (25%), and 602 (18%), and 8% ST-603 was present, but also many other small peaks.
7. The reaction was cooled to 22° C. (RT)
8. In a 100-mL beaker was prepared a quenching mixture of 7 g of solid $Na_2CO_3$ dissolved in 30 mL water and 10 mL of THF at RT.

9. To the above beaker was slowly added (over 10 min) the content of the reaction flask. Weak exotherm was observed but strong smell of H$_2$S gas.
10. The resulting mixture was stirred over 12 hours to completely quench the reaction (in a very high vent hood attached to a scrubber for safety). Lots of insolubles are visible at the end of the 12 hours.
11. The reaction slurry was passed through a 1" celite bed to remove fine insolubles. Very difficult filtration, so left for over 12 hours.
12. After finally getting two phase filtrate, the organic layer was separated (both are colored brown), dried over 2 g anhydrous sodium sulfate and concentrated on a rotovap at ≤50° C. to 20 mL volume. No solid ppt was observed during concentration.
13. The resulting solution was diluted with 20 mL of methanol and stirred at RT for 2 h.
14. No solids were observed, so added 20 mL of cold heptane. Still no solids. Left in refrigerator for 24 hrs but still no solids formed.

Example 11—Synthesis of crude 4-methyl-5-(pyrazin-2-yl)-3H-1,2-dithiole-3-thione, ST-617 (Step 3)

Aim: Carry out Step 3 to study cyclization of crude mixture from sodium pentanoate condensation.
Procedure
1. Added 5.65 g (0.025 mole) of P$_2$S$_5$ and 50 mL of Toluene into a 100-mL 2-neck RBF under nitrogen.
2. Yellow slurry.
3. Added crude ST-602-003 solution (~5 mL). Brown stirrable slurry
4. Started stirring and heated to 50° C. Slight color change to reddish hue. Slow H$_2$S gas evolution is observed which is passed through a caustic bubbler and no H$_2$S is exited.
5. Continued heating up to 95° C. and let stir for 36 hours.
6. A sample was taken for HPLC (method ST-1): 601 (10%) and 602 (17%) and 43% ST-603 was present, but also many other small peaks.
7. The reaction was cooled to 22° C. (RT)
8. In a 100-mL beaker was prepared a quenching mixture of 7 g of solid Na$_2$CO$_3$ dissolved in 30 mL water and 10 mL of THF at RT.
9. To the above beaker was slowly added (over 10 min) the content of the reaction flask. Weak exotherm was observed and some smell of H$_2$S gas.
10. The resulting mixture was stirred over 12 hours to completely quench the reaction (in a very high vent hood attached to a scrubber for safety). Some insolubles are visible at the end of the 12 hours.
11. The reaction slurry was passed through a 1" celite bed to remove fine insolubles. Difficult filtration over 6 hour period.
12. Two phase filtrate both red/brown in color—the organic layer was separated, dried over 2 g anhydrous sodium sulfate and concentrated on a rotovap at ≤50° C. to 20 mL volume. No solid ppt was observed during concentration.
13. The resulting solution was diluted with 20 mL of methanol and stirred at RT for 2 h.
14. No solids were observed, so added 20 mL of cold heptane. Still no solids. Left in refrigerator for 24 hrs, but still no solids formed.

Example 12—Alternative synthesis of methyl 2-methyl-3-oxo-3-(pyrazin-2-yl)propanoate, ST-602 (Step 2)

Aim: Replace base in Step 2 with excess sodium pentanoate
Procedure
1. Add 9 g (0.0724 mole) of sodium pentanoate (MWt 124) powder and 25 mL of dry THF into a 100-mL 2-neck RBF at 0° C. Stirred for 5 minutes
2. Added 2.9 g (0.0326 mole) of methyl propionate (Mwt 88) into the flask using a dropping funnel over 15 minutes. Color turned yellow.
3. Stirred for an additional 15 minutes at 0° C.
4. Add 2.5 g (0.0181 mole) of ST-601 was dissolved in 10 mL of THF and added into the reaction over 30 minutes while allowing the reaction to come to RT (~½, hr). No gas evolution or exotherm.
5. Stirred at reflux for 24 hours
6. Monitored by HPLC (Method ST1). After 24 hrs at reflux the reaction is a yellow-brown slurry
7. HPLC showed two peaks for ST-602 totaling 72.4%, and 12.1% of ST-601 and with an intermediate peak of 8.3% (all area % peaks) and many small peaks that were not present in baseline experiment
8. After 72 hrs at reflux the reaction is a dark brown slurry.
9. HPLC shows two peaks for ST-602 totaling 77.5%, and 9.2% of ST-601 with an intermediate peak of 4.1% (all area % peaks) and same smaller peaks.
10. Concentrated on a rotovap at ≤50° C. to ~5 mL
11. The dark brown solution may be used as is in P$_2$S$_5$ cyclization step.
12. Labeled as ST-602-008

Example 13—Synthesis of crude 4-methyl-5-(pyrazin-2-yl)-3H-1,2-dithiole-3-thione, ST-617 (Step 3)

Aim: Carry out Step 3 to study cyclization of crude mixture from sodium pentanoate Condensation.
Procedure
1. Added 5.65 g (0.025 mole) of P$_2$S$_5$ and 50 mL of Toluene into a 100-mL 2-neck RBF under nitrogen.
2. Thick, yellow slurry.
3. Added crude ST-602-003 solution (~5 mL). Brown, stirrable slurry
4. Started stirring and heated to 50° C. Slight color change to red-brown. Slow H$_2$S gas evolution was observed, which was passed through a caustic bubbler and no H$_2$S was exited.
5. Continued heating up to 95° C. and let stir for 36 hours.
6. A sample was taken for HPLC (method ST-1): 601 (10%) and 602 (17%) and 43% ST-603 was present, but also many other small peaks.
7. The reaction was cooled to 22° C. (RT)
8. In a 100-mL beaker was prepared a quenching mixture of 7 g of solid Na$_2$CO$_3$ dissolved in 30 mL water and 10 mL of THF at RT.
9. To the above beaker was slowly added (over 10 min) the content of the reaction flask. Weak exotherm was observed and some smell of H$_2$S gas.
10. The resulting mixture was stirred over 12 hours to completely quench the reaction (in a very high vent hood attached to a scrubber for safety). Some insolubles were visible at the end of the 12 hours.
11. The reaction slurry was passed through a 1" celite bed to remove fine insolubles. Difficult filtration over 6 hour period.

12. Two phase filtrate both red/brown in color—the organic layer was separated, dried over 2 g anhydrous sodium sulfate, and concentrated on a rotovap at ≤50° C. to 20 mL volume. No solid ppt was observed during concentration.
13. The resulting solution was diluted with 20 mL of methanol and stirred at RT for 2 h.
14. No solids were observed, so added 20 mL of cold heptane. Still no solids. Left in refrigerator for 24 hrs and some solids were visible.
15. Reduced the volume to 5 mL on a rotovap and added fresh cold 20 mL heptane. Left in refrigerator overnight.
16. The solids were collected by filtration, rinsed 2× with 20 mL of refrigerated cold methanol followed by 20 mL of cold heptane.
18. Dried in vacuum oven to constant weight.
19. Weight of Powder is 139 mg (·4.8% yield)
20. HPLC shows 94.8% ST-617 product against authentic sample.
21. Labelled as ST-603-009

Example 14—Alternative synthesis of methyl 2-methyl-3-oxo-3-(pyrazin-2-yl)propanoate, ST-602 (Step 2)

Aim: Replace base in Step 2 with 2× sodium pentanoate
Procedure
1. Add 4.5 g (0.0362 mole) of sodium pentanoate (MWt 124) powder and 25 mL of dry THF into a 100-mL 2-neck RBF at 0° C. Stirred for 5 minutes
2. Added 2.9 g (0.0326 mole) of methyl propionate (Mwt 88) into the flask using a dropping funnel over 15 minutes. Color turned yellow.
3. Stirred for an additional 15 minutes at 0° C.
4. 2.5 g (0.0181 mole) of ST-601 was dissolved in 10 mL of THF and added into the reaction over 30 minutes while allowing the reaction to come to RT (~½ hr). No gas evolution or exotherm.
5. Stirred for 24 hours at RT
6. TLC shows product (ST-602) spot (Rf 0.4) begins forming after 2 hrs at RT and an intermediate spot (Rf 0.2) and spot for ST-601 is still also visible. Second 2 hr TLC shows more product spot but still shows both intermediate and ST-601 spots. After 6 hrs ST-602 spot and only trace of intermediate and ST-601. Stirred overnight. After 16 hrs no change from 6 hr TLC.
7. 20 mL of distilled water and 20 mL of saturated sodium chloride solution were added to the reaction solution and stirred for 30 minutes.
8. The reaction solution was concentrated to a volume of 40 mL and then extracted with 2×25 mL of toluene.
9. The resultant extract was dried over anhydrous magnesium sulfate and filtered
10. The filtrate was rotovaped to give 1.9 g crude ST-602 as a dark brown viscous oil
11. Labeled as ST-602-010

Example 15—Alternative synthesis of methyl 2-methyl-3-oxo-3-(pyrazin-2-yl)propanoate, ST-602 (Step 2)

Aim: Replace base in Step 2 with 2× sodium pentanoate and vary temperature procedure
1. Add 4.5 g (0.0362 mole) of sodium pentanoate (Mwt 124) powder and 25 mL of dry THF into a 100-mL 2-neck RBF at 0° C. Stirred for 5 minutes
2. Added 2.9 g (0.0326 mole) of methyl propionate (Mwt 88) into the flask using a dropping funnel over 15 minutes. Color turned yellow.
3. Stirred for an additional 15 minutes at 0° C.
4. Add 2.5 g (0.0181 mole) of ST-601 was dissolved in 10 mL of THF and added into the reaction over 30 minutes while allowing the reaction to come to RT(~½ hr). No gas evolution or exotherm.
5. Warmed to 40° C.
6. Monitored on TLC every 2 hours
7 TLC showed product (ST-602) spot (Rf 0.4) after 2 hrs at RT with almost no ST-601 but a long streaking along the plate.
8. Continued at 40° C. to complete the experiment for 6 hrs
9. 20 mL of distilled water and 20 mL of saturated sodium chloride solution were added to the reaction solution and stirred for 30 minutes.
10. The reaction solution was concentrated to a volume of 45 mL and then extracted with 2×25 mL of toluene
11. The resultant extract was almost black in color and had suspended solids and was very tarry in form
15. Labeled as ST-602-011 but kept for discard.

Example 16—Alternative synthesis of methyl 2-methyl-3-oxo-3-(pyrazin-2-yl)propanoate, ST-602 (Step 2)

Aim: Replace base in Step 2 with 2× sodium pentanoate, use warmer temperature for formation of anion, and stop reaction after 6 h
Procedure
1. Add 4.5 g (0.0362 mole) of sodium pentanoate (MWt 124) powder and 25 mL of dry THF into a 100-mL 2-neck RBF at 10° C. Stirred for 5 minutes
2. Added 2.9 g (0.0326 mole) of methyl propionate (MWt 88) into the flask using a dropping funnel over 15 minutes. Color turned yellow.
3. Stirred for an additional 15 minutes at 10° C.
4. Add 2.5 g (0.0181 mole) of ST-601 was dissolved in 10 mL of THF and added into the reaction over 30 minutes while allowing the reaction to come to RT (~½ hr). No gas evolution or exotherm.
5. Stirred at RT for 6 hours. Monitor on TLC every 2 hours
6. TLC showed product (ST-602) spot (Rf 0.4) begins forming after 2 hrs at RT and an intermediate spot (Rf 0.2) and spot for ST-601 is still also visible. Second 2 hr TLC showed more product spot but still showed both intermediate and ST-601 spots. After 6 hrs ST-602 spot and only trace of intermediate and ST-601 is visible.
7. 20 mL of distilled water and 20 mL of saturated sodium chloride solution were added to the reaction solution and stirred for 30 minutes
8. The reaction solution was concentrated to a volume of 45 mL and then extracted with 2×25 mL of toluene.
9. The resultant extract was dried over anhydrous magnesium sulfate and filtered.
10. The filtrate was rotovaped to give 2.7 g crude ST-602 as a brown oil with no tarry nature.
11. Labeled as ST-602-012 and carried forward for cyclization experiment

Example 17—Synthesis of crude 4-methyl-5-(pyrazin-2-yl)-3H-1,2-dithiole-3-thione, ST-617
(Step 3)

Aim: Carry out Step 3 using the solvent system described in U.S. Pat. No. 7,288,652 to establish baseline Procedure 1. Added 5.65 g (0.025 mole) of $P_2S_5$ and 25 mL Toluene+25 mL mixed xylenes into a 100-mL 2-neck RBF under nitrogen.
2. Yellow slurry but easily stirrable.
3. Heated to 120° C. while stirring
4. Added crude ST-602-012 solution (~10 mL in toluene). Yellow-brown slurry.
5. Started stirring and heated to reflux (~140° C.). Color changes to reddish brown in 5 mins. Slow $H_2S$ gas evolution was observed, which was passed through a caustic bubbler and no $H_2S$ is exited.
6. Continued reflux for 6 hours.
7. A sample was taken for HPLC (method ST-1): no starting material present, and product ST-603 was present but also some other small peaks.
8. The reaction was cooled to 25° C. (RT)
9. In a 100-mL beaker was prepared a quenching mixture of 7 g of solid $Na_2CO_3$ dissolved in 30 mL water and 10 mL of THF at RT.
10. To the above beaker was slowly added (over 10 min) the content of the reaction flask. Weak exotherm was observed but no $H_2S$ gas smell at all.
11. The resulting mixture was stirred over 3 hours to complete quench of the reaction (in a very high vent hood attached to a scrubber for safety). Very few insolubles are visible at the end of the 3 hours.
12. The reaction slurry was passed through a 1" celite bed to remove the fine insolubles.
13. The organic layer was separated (both are colored red), dried over 2 g anhydrous sodium sulfate, and concentrated on a rotovap at ≤50° C. to 20 mL volume.
14. The resulting slurry was diluted with 20 mL of methanol and stirred at RT for 2 h resulting in solids
15. The solids were collected by filtration, rinsed 2× with 20 mL of refrigerated cold methanol followed by 20 mL of cold heptane.
16. Dried in vacuum oven to constant weight.
17. Weight of crude ST-603 crystalline powder is 609 mg (~21% yield)
18. Labelled as ST-603-013.

Example 18—Alternative synthesis of methyl 2-methyl-3-oxo-3-(pyrazin-2-yl)propanoate, ST-602
(Step 2)

Aim: Replace base in Step 2 with 2× sodium pentanoate, use 15% 1,4-dioxane in THF as solvent system for reaction Procedure 1. Added 4.5 g (0.0362 mole) of sodium pentanoate (MWt 124) powder and 25 mL of dry THF into a 100-mL 2-neck RBF at 0° C. Stirred for 5 minutes
2. Added 2.9 g (0.0326 mole) of methyl propionate (Mwt 88) into the flask using a dropping funnel over 15 minutes. Color turns yellow.
3. Stirred for an additional 15 minutes at 0° C.
4. 2.5 g (0.0181 mole) of ST-601 was dissolved in 5 mL of THF+5 mL of 1,4-Dioxane and added into the reaction over 30 minutes while allowing the reaction to come to RT (~½ hr). No gas evolution or exotherm.
5. Stirred at RT for 6 hours. Monitored by TLC every 2 hours.
6. TLC shows product (ST-602) spot (Rf 0.4) begins forming after 2 hrs at RT and an intermediate spot (Rf 0.2) and spot for ST-601 is still also visible. Second 2 hr TLC shows more product spot but still shows both intermediate and ST-601 spots. After 6 hrs, ST-602 spot and only trace of intermediate and ST-601 spots were visible.
7. 30 mL of distilled water and 30 mL of saturated sodium chloride solution were added to the reaction solution (extra aqueous layer added due to more polar 1,4-dioxane and stirred for 30 minutes.
8. The reaction solution was concentrated to a volume of 60 mL and then extracted with 2×25 mL of toluene.
9. The resultant extract was dried over anhydrous magnesium sulfate and filtered.
10. The filtrate was rotovaped to give 3.1 g crude ST-602 as a brown oil with no tarry nature
11. Labeled as ST-602-014 (GC shows 84% ST-002 peak)

Example 19—Alternative synthesis of methyl 2-methyl-3-oxo-3-(pyrazin-2-yl)propanoate, ST-602
(Step 2)

Aim: Replace base in Step 2 with 2× sodium pentanoate, use 1,4-dioxane as solvent system for reaction Procedure 1. Added 4.5 g (0.0362 mole) of sodium pentanoate (Mwt 124) powder and 25 mL of dry 1,4-dioxane into a 100-mL 2-neck RBF at 0° C. Stirred for 5 minutes
2. Added 2.9 g (0.0326 mole) of methyl propionate (Mwt 88) into the flask using a dropping funnel over 15 minutes. Color turned yellow.
3. Stirred for an additional 15 minutes at 0° C.
4. 2.5 g (0.0181 mole) of ST-601 was dissolved in 10 mL of 1,4-Dioxane and added into the reaction over 30 minutes while allowing the reaction to come to RT (~½ hr). No gas evolution or exotherm.
5. Stirred at RT for 6 hours. Monitored by TLC every 2 hours.
6. TLC showed product (ST-602) spot (Rf 0.4) begins forming after 2 hrs at RT but multiple new trailing spots also present. After 6 hrs, ST-602 spot, no ST-601 but lots of multiple smaller spots were visible.
7. 50 mL of distilled water and 50 mL of saturated sodium chloride solution were added to the reaction solution (extra aqueous layer added due to more polar 1,4-dioxane) and stirred for 30 minutes.
8. The reaction solution was concentrated to a volume of 100 mL (using a high vacuum on the rotovap) and then extracted with 2×25 mL of toluene
9. The resultant extract was dried over anhydrous magnesium sulfate and filtered
10. The filtrate was rotovaped to give 1.8 g crude ST-602 as a brown oil with some tarry nature
11. Labeled as ST-602-015 (GC shows 68% ST-002 peak)

Example 20—Alternative synthesis of methyl 2-methyl-3-oxo-3-(pyrazin-2-yl)propanoate, ST-602
(Step 2)

Aim: Replace base in Step 2 with 2× sodium pentanoate, use 1,4-dioxane as solvent system for reaction, complete reaction at 0° C.

Procedure
1. Added 4.5 g (0.0362 mole) of sodium pentanoate (MWt 124) powder and 25 mL of dry 1,4-dioxane into a 100-mL 2-neck RBF at 0° C. Stirred for 5 minutes
2. Added 2.9 g (0.0326 mole) of methyl propionate (Mwt 88) into the flask using a dropping funnel over 15 minutes. Color turned yellow.
3. Stirred for an additional 15 minutes at 0° C.
4. 2.5 g (0.0181 mole) of ST-601 was dissolved in 10 mL of 1,4-Dioxane and added into the reaction over 30 minutes. No gas evolution or exotherm.
5. Stirred at 0° C. for 6 hours. Monitored by TLC every 2 hours.
6. TLC shows a small amount of product (ST-602) spot (Rf 0.4) began forming after 2 hrs at RT. Intermediate spot was visible and large ST-601 spot. After 4 hrs, no real change in TLC. Skipped the 6 hr TLC and stirred overnight (12 hrs) at 0° C. TLC now shows more ST-602 but still ~20% ST-601 was visible. Allowed the reaction to warm up to 10° C. and stirred for 2 hrs more. All the ST-601 was gone, many trialing spots were visible so reaction was taken for workup.
7. 50 mL of distilled water and 50 mL of saturated sodium chloride solution were added to the reaction solution (extra aqueous layer added due to more polar 1,4-dioxane) and stirred for 30 minutes
8. The reaction solution was concentrated to a volume of 110 mL (using a high vacuum on the rotovap) and then extracted with 2×25 mL of toluene.
9. The resultant extract was dried over anhydrous magnesium sulfate and filtered
10. The filtrate was rotovaped to give 2.0 g crude ST-602 as a brown oil with almost no tarry nature.
11. Labeled as ST-602-016 (GC showed 71% ST-002 peak)

Example 21—Alternative synthesis of methyl 2-methyl-3-oxo-3-(pyrazin-2-yl)propanoate, ST-602 (Step 2)

Aim: Replace base in Step 2 with 2× sodium pentanoate, use 30% 1,4-dioxane in THF as solvent system for reaction
Procedure
1. Added 4.5 g (0.0362 mole) of sodium pentanoate (MWt 124) powder and 20 mL of dry THF+5 mL 1,4-dioxane into a 100-mL 2-neck RBF at 0° C. Stirred for 5 minutes
2. Added 2.9 g (0.0326 mole) of methyl propionate (Mwt 88) into the flask using a dropping funnel over 15 minutes. Color turned pale yellow.
3. Stirred for an additional 15 minutes at 0° C. No color change.
4. 2.5 g (0.0181 mole) of ST-601 was dissolved in 5 mL of THF+5 mL of 1,4-Dioxane and added into the reaction over 30 minutes while allowing the reaction to come to RT (~½ hr). No gas evolution or exotherm.
5. Stirred at RT for 6 hours. Monitored by TLC every 2 hours.
6. TLC showed ~60% product (ST-602) spot (Rf 0.4) began forming after 2 hrs at RT and an intermediate spot (Rf 0.2) and ≤10% spot for ST-601 was still also visible. Second 2 hr TLC showed more product spot and intermediate spot but no ST-601 spot. After 6 hrs ST-602 spot only and some trailing spots visible.
7. 30 mL of distilled water and 30 mL of saturated sodium chloride solution were added to the reaction solution and stirred for 30 minutes
8. The reaction solution was concentrated to a volume of 65 mL (vacuum of 14 mmHg was adequate on rotovap) and then extracted with 2×30 mL of toluene
9. The resultant extract was dried over anhydrous magnesium sulfate and filtered.
10. The filtrate was rotovaped to give 3.3 g crude ST-602 (MWt=194) as a brown oil with no tarry nature
11. Labeled as ST-602-017 to be carried forward for cyclization experiment Example 22—Alternative synthesis of methyl 2-methyl-3-oxo-3-(pyrazin-2-yl)propanoate, ST-602 (Step 2)

Aim: Replace base in Step 2 with 2× potassium t-butoxide, use 30% 1,4-dioxane in THF as solvent system for reaction
Procedure
1. Added 4.1 g (0.0362 mole) of potassium t-butoxide powder (MWt 112) powder and 20 mL of dry THF+5 mL 1,4-dioxane into a 100-mL 2-neck RBF at 0° C. Stirred for 5 minutes
2. Added 2.9 g (0.0326 mole) of methyl propionate (Mwt 88) into the flask using a dropping funnel over 15 minutes. Color turned pale yellow.
3. Stirred for an additional 15 minutes at 0° C. No color change.
4. 2.5 g (0.0181 mole) of ST-601 was dissolved in 5 mL of THF+5 mL of 1,4-Dioxane and added into the reaction over 30 minutes while allowing the reaction to come to RT (~½ hr). No gas evolution or exotherm.
5. Stirred at RT for 6 hours. Monitor on TLC every 2 hours.
6. Very similar TLC profile as previous Example. TLC showed ~60% product (ST-602) spot (Rf 0.4) began forming after 2 hrs at RT and an Intermediate spot (Rf 0.2) and ≤10% spot for ST-601 was still also visible. Second 2 hr TLC showed more product spot and intermediate spot but no ST-601 spot.
7. 30 mL of distilled water and 30 mL of saturated sodium chloride solution were added to the reaction solution and stirred for 30 minutes.
8. The reaction solution was concentrated to a volume of 65 mL (vacuum of 14 mmHg was adequate on rotovap) and then extracted with 2×30 mL of toluene.
9. The resultant extract was dried over anhydrous magnesium sulfate and filtered.
10. The filtrate was rotovaped to give 3.1 g crude ST-602 (MWt=194) as a brown oil with no tarry nature.
11. Labeled as ST-602-018 will be carried forward for cyclization experiment Example 23—Synthesis of crude 4-methyl-5-(pyrazin-2-yl)-3H-1,2-dithiole-3-thione, ST-617 (Step 3)

Aim: Carry out Step 3 to study cyclization of much cleaner crude mixture from condensation.
Procedure
1. Added 5.65 g (0.025 mole) of $P_2S_5$ and 50 mL Toluene into a 100-mL 2-neck RBF under nitrogen.
2. Yellow slurry but easily stirrable.
3. Heated to 100° C. while stirring
4. Added crude ST-602-019a solution (12.4 g solution in toluene). Yellow-brown slurry.
5. Started stirring and heated to reflux (~110° C.). Color changed to reddish brown in 15 mins. Slow $H_2S$ gas evolution was observed which is passed through a caustic bubbler and no $H_2S$ is exited.

6. Continued reflux for 6 hours.
7. A sample was taken for HPLC (method ST-1). No starting material present. Product ST-603 was present but also some other small peaks.
8. The reaction was cooled to 25° C. (RT)
9. In a 100-mL beaker was prepared a quenching mixture of 7 g of solid $Na_2CO_3$ dissolved in 30 mL water and 10 mL of THF at RT.
10. To the above beaker was slowly added (over 10 min) the contents of the reaction flask. Weak exotherm was observed but no $H_2S$ gas smell at all.
11. The resulting mixture was stirred over 3 hours to complete quench of the reaction (in a very high vent hood attached to a scrubber for safety). Very few insolubles are visible at the end of the 3 hours.
12. The reaction slurry was passed through a 1" celite bed to remove the fine insolubles. Much more easily filtered than comparative ST-603-005.
13. The organic layer was separated (both are colored red), dried over 2 g anhydrous sodium sulfate, and concentrated on a rotovap at ≤50° C. to 20 mL volume.
14. The resulting slurry was diluted with 20 mL of methanol and stirred at RT for 2 h resulting in solids
15. The solids were collected by filtration, rinsed 2× with 20 mL of refrigerated cold methanol followed by 20 mL of cold heptane.
16. Dried in vacuum oven to constant weight.
17. Weight of crude ST-603 crystalline powder is 874 mg (~21% yield) (Mol Wt=226) GC=97.3%
18. Labelled as ST-603-020.

Example 24—Synthesis of Crude 4-methyl-5-(pyrazin-2-yl)-3H-1,2-dithiole-3-thione, ST-617 (Step 3)

Aim: Carry out Step 3 to study cyclization of much cleaner crude mixture from condensation using solvent system and slightly higher reflux temperature from U.S. Pat. No. 7,288,652

Procedure
1. Added 5.65 g (0.025 mole) of $P_2S_5$ and 25 mL toluene+ 30 mL xylene into a 100-mL 2-neck RBF under nitrogen.
2. Yellow slurry but easily stirred.
3. Heated to 130° C. while stirring
4. Added crude ST-602-019b solution (~10 mL in toluene). Yellow-brown slurry.
5. Started stirring and heated to reflux (~110° C.). Color changed to reddish brown in 15 mins. Slow $H_2S$ gas evolution is observed which is passed through a caustic bubbler and no $H_2S$ is exited.
6. Continued reflux for 6 hours.
7. A sample was taken for HPLC (method ST-1). No starting material present. Product ST-603 is present but also some other small peaks.
8. The reaction was cooled to 25° C. (RT)
9. In a 100-mL beaker was prepared a quenching mixture of 7 g of solid $Na_2CO_3$ dissolved in 30 mL water and 10 mL of THF at RT.
10. To the above beaker was slowly added (over 10 min) the contents of the reaction flask. Weak exotherm was observed but no $H_2S$ gas smell at all.
11. The resulting mixture was stirred over 3 hours to complete quench of the reaction (in a very high vent hood attached to a scrubber for safety). Very few insolubles are visible at the end of the 3 hours.
12. The reaction slurry was passed through a 1" celite bed to remove the fine insolubles. easy filtration may even work with paper.
13. The organic layer was separated (both are colored red), dried over 2 g anhydrous sodium sulfate, and concentrated on a rotovap at ≤50° C. to 20 mL volume.
14. The resulting slurry was diluted with 20 mL of methanol and stirred at RT for 2 h resulting in solids
15. The solids were collected by filtration, rinsed 2× with 20 mL of refrigerated cold methanol followed by 20 mL of cold heptane.
16. Dried in vacuum oven to constant weight.
17. Weight of crude ST-603 crystalline powder is 826 mg—very similar and within error of the yield produced by the method of the previous Example, so apparently the higher boiling point does not materially affect to the reaction yield.
18. Labelled as ST-603-021.

Example 25—Synthesis of methyl 2-methyl-3-oxo-3-(pyrazin-2-yl)propanoate, ST-602 (Step 2)

Aim: Replace base in Step 2 with 2× potassium t-butoxide, as described in U.S. Pat. No. 7,288,652

Procedure
1. Added 4.1 g (0.0362 mole) of potassium t-butoxide powder (MWt 112) powder and 25 mL of dry THF into a 100-mL 2-neck RBF at 0° C. Stirred for 5 minutes
2. Added 2.9 g (0.0326 mole) of methyl propionate (Mwt 88) into the flask using a dropping funnel over 15 minutes. Color turned pale yellow.
3. Stirred for an additional 15 minutes at 0° C. No color change.
4. 2.5 g (0.0181 mole) of ST-601 was dissolved in 10 mL of THF and added into the reaction over 30 minutes while allowing the reaction to come to RT (~½ hr). No gas evolution or exotherm.
5. Stirred at RT for 6 hours. Monitored by TLC every 2 hours.
6. TLC shows ~60% product (ST-602) spot (Rf 0.4) began forming after 2 hrs at RT and an intermediate spot (Rf 0.2) and ≤10% spot for ST-601 was still also visible. Second 2 hr TLC showed more product spot and intermediate spot but no ST-601 spot.
7. 30 mL of distilled water and 30 mL of saturated sodium chloride solution were added to the reaction solution and stirred for 30 minutes.
8. The reaction solution was concentrated to a volume of 65 mL (vacuum of 14 mmHg was adequate on rotovap) and then extracted with 2×30 mL of toluene.
9. The resultant extract was dried over anhydrous magnesium sulfate and filtered.
10. The filtrate was rotovaped to give 2.7 g crude ST-602 (MWt=194) as a brown oil with little tarry nature.
11. Labeled as ST-602-022 will be carried forward for cyclization experiment as per U.S. Pat. No. 7,288,652 for total yield comparisons.

Example 26—Synthesis of crude 4-methyl-5-(pyrazin-2-yl)-3H-1,2-dithiole-3-thione, ST-617 (Step 3)

Aim: Carry out Step 3 to study overall yield an purity of Steps 1, 2, and 3 as described in U.S. Pat. No. 7,288,652

Procedure
1. Added 5.65 g (0.025 mole) of $P_2S_5$ and 25 mL toluene+ 30 mL xylene into a 100-mL 2-neck RBF under nitrogen.
2. Yellow slurry but easily stirred.
3. Heated to 130° C. while stirring
4. Added crude ST-602-019b solution HO mL in toluene). Yellow-brown slurry.
5. Started stirring and heated to reflux (~110° C.). Color changed to reddish brown in 15 mins. Slow $H_2S$ gas evolution was observed which is passed through a caustic bubbler and no $H_2S$ is exited.
6. Continued reflux for 6 hours.
7. A sample was taken for HPLC (method ST-1). No starting material present. Product ST-603 was present but also some other small peaks.
8. The reaction was cooled to 25° C. (RT)
9. In a 100-mL beaker was prepared a quenching mixture of 7 g of solid $Na_2CO_3$ dissolved in 30 mL water and 10 mL of THF at RT.
10. To the above beaker was slowly added (over 10 min) the content of the reaction flask. Weak exotherm was observed but no $H_2S$ gas smell at all.
11. The resulting mixture was stirred over 3 hours to complete quench of the reaction (in a very high vent hood attached to a scrubber for safety). Very few insolubles are visible at the end of the 3 hours.
12. The reaction slurry was passed through a 1" celite bed to remove the fine insolubles. easy filtration may even work with paper.
13. The organic layer was separated (both are colored red), dried over 2 g anhydrous sodium sulfate, and concentrated on a rotovap at ≤50° C. to 20 mL volume.
14. The resulting slurry was diluted with 20 mL of methanol and stirred at RT for 2 h resulting in solids
15. The solids were collected by filtration, rinsed 2× with 20 mL of refrigerated cold methanol followed by 20 mL of cold heptane.
16. Dried in vacuum oven to constant weight.
17. Weight of crude ST-603 crystalline powder was 708 mg. Labelled as ST-603-023. GC shows purity of 96.7%.

Example 27—Catalyzed synthesis of crude 4-methyl-5-(pyrazin-2-yl)-3H-1,2-dithiole-3-thione, ST-617 (Step 3)

Aim: Carry out Step 3 using tetrabutyl phosphonium chloride in toluene+water
Procedure
1. Added 5.65 g (0.025 mole) of $P_2S_5$ and 50 mL Toluene+5 mL water into a 100-mL 2-neck RBF under nitrogen.
2. Yellow slurry but easily stirrable.
3. Added 100 mg of tetrabutyl phosphonium chloride
4. Heated to 100° C. while stirring
5. Added crude ST-602-034a solution (12 g solution in toluene). Yellow-Green slurry.
6. Started stirring and heated to reflux (~110° C.). Color changed to red-brown after 20 min. Some $H_2S$ gas evolution was observed which was passed through a caustic bubbler and no $H_2S$ was exited.
7. Continued reflux for 2 hours.
8. A sample was taken for TLC. ~50% starting material present. Product ST-603 is also present but some other spots also present.
9. Continued reflux for 2 hours.
10. A sample was taken for TLC. <5% starting material present. Product ST-603 is also present but some other spots also present.
11. The reaction was cooled to 25° C. (RT)
12. In a 100-mL beaker was prepared a quenching mixture of 7 g of solid $Na_2CO_3$ dissolved in 30 mL water and 10 mL of THF at RT.
13. To the above beaker was slowly added (over 10 min) the content of the reaction flask. No exotherm was observed and no $H_2S$ gas smell at all.
14. The resulting mixture was stirred for 2 hours to complete quench of the reaction (in a very high vent hood attached to a scrubber for safety). Some insolubles are visible at the end of the 2 hours.
15. The reaction slurry was passed through a 1" celite bed to remove the fine insolubles. Slow filtration.
16. The organic layer was separated (both were colored red-brown), dried over 2 g anhydrous sodium sulfate and concentrated on a rotovap at ≤50° C. to 20 mL volume.
17. The resulting slurry was diluted with 20 mL of methanol and stirred at RT for 2 h resulting in sticky solids only but titutration with hexane did yield approx. 400 mg of flowable red-brown powder. TLC shows mostly ST-603—sample saved as ST-603-35.

Example 28—Synthesis of crude 4-methyl-5-(pyrazin-2-yl)-3H-1,2-dithiole-3-thione, ST-617 (Step 3)

Aim: Carry out Step 3 in toluene under reflux pressure
Procedure
1. Added 5.65 g (0.025 mole) of $P_2S_5$ and 50 mL toluene into a 200 mL SS316 autoclave under nitrogen.
2. Added crude ST-602-019d solution (~10 mL in toluene). Yellow-brown slurry.
3. Started stirring, sealed the autoclave, and heated to jacket temperature 180° C.
4. Pressure gauge showed increasing pressure from 1 ATM to 16.4 ATM after 2 hours and held steady.
5. Continued 2 additional hours for a total of 4 hours.
6. Released the pressure into a caustic bubbler.
7. In a 100-mL beaker was prepared a quenching mixture of 7 g of solid $Na_2CO_3$ dissolved in 30 mL water and 10 mL of THF at RT.
8. To the above beaker was slowly added (over 10 min) the contents of the reaction flask. Weak exotherm was observed and some $H_2S$ gas could be detected by smell.
9. The resulting mixture was stirred over 3 hours to complete quench of the reaction (in a very high vent hood attached to a scrubber for safety). Few insolubles were visible at the end of the 3 hours.
10. The reaction slurry was passed through a 1" celite bed to remove the fine insolubles.
11. The organic layer was separated (both layers were colored red), dried over 2 g anhydrous sodium sulfate, and concentrated on a rotovap at ≤50° C. to 20 mL volume.
12. The resulting slurry was diluted with 20 mL of methanol and stirred at about 23° C. (room temperature or RT) for 2 h, resulting in solids.
13. The solids were collected by filtration, rinsed 2× with 20 mL of refrigerated cold methanol, followed by 20 mL of cold heptane.
14. Dried in vacuum oven to constant weight.

15. Weight of crude ST-603 brown pasty powder is 943 mg. TLC showed the product spot but many other smaller spots. Labelled as ST-603-024. GC purity=64.3%.

Example 29—Synthesis of methyl 2-methyl-3-oxo-3-(pyrazin-2-yl)propanoate, ST-602 (Step 2)

Aim: Scale-up Step 2
Procedure
1. Add 32.8 g (0.2896 mole) of potassium t-butoxide powder and 160 mL of dry THF+40 mL 1,4-dioxane into a 500-mL 2-neck RBF at 0° C. Stirred for 5 minutes
2. Added 23.2 g (0.2608 mole) of methyl propionate into the flask using a dropping funnel over 15 minutes. Color turned pale yellow.
3. Stirred for an additional 15 minutes at 0° C. No color change.
4. Added 20 g (0.1448 mole) of ST-601 dissolved in 40 mL of THF+40 mL of 1,4-dioxane over 30 minutes while allowing the reaction to come to RT. No gas evolution or exotherm was observed.
5. Stirred at RT for 12 hours. Monitored by TLC every 2 hours.
6. 240 mL of distilled water and 240 mL of saturated sodium chloride solution were added to the reaction solution, which was subsequently stirred for 30 minutes.
7. The reaction solution was concentrated to a volume of 510 mL (vacuum of 14 mmHg was adequate on rotovap) and then extracted with 2×240 mL of toluene.
8. The resultant extract was rotovaped to give 97.7 g crude ST-602 as a brown oil with no tarry nature.
9. The solution was divided into eight equal parts and labelled as ST-602-25a, b, c, d, e f, g, h for comparative cyclization experiments.

Example 30—Synthesis of crude 4-methyl-5-(pyrazin-2-yl)-3H-1,2-dithiole-3-thione, ST-617 (Step 3)

Aim: Carry out Step 3 in toluene in autoclave under reflux
Procedure
1. Added 5.65 g (0.025 mole) of $P_2S_5$ and 50 mL toluene into a 200-mL SS316 autoclave under nitrogen.
2. Added crude ST-602-025a solution (~10 mL in toluene). Yellow-brown slurry.
3. Started stirring, sealed the autoclave, and heated to jacket temperature 180° C.
4. Pressure gauge showed increasing pressure from 1 ATM to 16.1 ATM after 2 hours and held steady.
5. Released the pressure into a caustic bubbler.
6. In a 100-mL beaker was prepared a quenching mixture of 7 g of solid $Na_2CO_3$ dissolved in 30 mL water and 10 mL of THF at RT.
7. To the above beaker was slowly added (over 10 min) the contents of the reaction flask. A weak exotherm was observed and some $H_2S$ gas was detected.
8. The resulting mixture was stirred over 3 hours to complete quench of the reaction (in a very high vent hood attached to a scrubber for safety). Few insolubles were visible at the end of the 3 hours.
9. The reaction slurry was passed through a 1" celite bed to remove the fine insolubles.
10. The organic layer was separated (both are colored red), dried over 2 g anhydrous sodium sulfate, and concentrated on a rotovap at ≤50° C. to 20 mL volume.
11. The resulting slurry was diluted with 20 mL of methanol and stirred at RT for 2 h, resulting in solids
12. The solids were collected by filtration, rinsed 2× with 20 mL of refrigerated cold methanol, followed by 20 mL of cold heptane.
13. Dried in vacuum oven to constant weight.
14. Weight of crude ST-603 brown pasty powder was 802 mg. TLC showed some product but also many less concentrated side products. Labelled as ST-603-026.

Example 31—Synthesis of crude 4-methyl-5-(pyrazin-2-yl)-3H-1,2-dithiole-3-thione, ST-617 (Step 3)

Aim: Carry out Step 3 in toluene in autoclave under reflux for 12 h
Procedure
1. Added 5.65 g (0.025 mole) of $P_2S_5$ and 50 mL toluene into a 200-mL SS316 autoclave under nitrogen.
2. Added crude ST-602-025b solution HO mL in toluene). Yellow-brown slurry.
3. Started stirring, sealed the autoclave, and heated to jacket temperature 180° C.
4. Pressure gauge showed increasing pressure from 1 ATM to 16.1 ATM after 2 hours and held steady.
5. Held under pressure overnight.
6. Released the pressure into a caustic bubbler.
7. In a 100-mL beaker was prepared a quenching mixture of 7 g of solid $Na_2CO_3$ dissolved in 30 mL water and 10 mL of THF at RT.
8. To the above beaker was slowly added (over 10 min) the contents of the reaction flask. A weak exotherm was observed and some $H_2S$ gas was detected.
9. The resulting mixture was stirred over 3 hours to complete quench of the reaction (in a very high vent hood attached to a scrubber for safety). Few insolubles were visible at the end of the 3 hours.
10. The reaction slurry was passed through a 1" celite bed to remove the fine insolubles.
11. The organic layer was separated (both are colored red), dried over 2 g anhydrous sodium sulfate, and concentrated on a rotovap at ≤50° C. to 20 mL volume.
12. The resulting slurry was diluted with 20 mL of methanol and stirred at RT for 2 h resulting in solids.
13. The solids were collected by filtration, rinsed 2× with 20 mL of refrigerated cold methanol followed by 20 mL of cold heptane.
14. Dried in vacuum oven to constant weight.
15. Weight of crude ST-603 brown pasty powder was 985 mg. TLC showed some product but many less concentrated side products were also visible. Labelled as ST-603-027. GC purity=54%.

Example 32—Synthesis of crude 4-methyl-5-(pyrazin-2-yl)-3H-1,2-dithiole-3-thione, ST-617 (Step 3)

Aim: Carry out Step 3 in xylene in autoclave under reflux
Procedure
1. Added 5.65 g (0.025 mole) of $P_2S_5$ and 50 mL xylene into a 200-mL SS316 autoclave under nitrogen.
2. Added crude ST-602-025c solution (~10 mL in toluene). Yellow-brown slurry.

3. Started stirring, sealed the autoclave and heated to jacket temperature 180° C.
4. Pressure gauge showed increasing pressure from 1 ATM to 15.1 ATM after 2 hours and held steady.
5. Continued 2 additional hours for a total of 4 hours.
6. Released the pressure into a caustic bubbler.
7. In a 100-mL beaker was prepared a quenching mixture of 7 g of solid $Na_2CO_3$ dissolved in 30 mL water and 10 mL of THF at RT.
8. To the above beaker was slowly added (over 10 min) the contents of the reaction flask. A weak exotherm was observed and some $H_2S$ gas was detected.
9. The resulting mixture was stirred over 3 hours to complete quench of the reaction (in a very high vent hood attached to a scrubber for safety). Few insolubles were visible at the end of the 3 hours.
10. The reaction slurry was passed through a 1" celite bed to remove the fine insolubles.
11. The organic layer was separated (both are colored red), dried over 2 g anhydrous sodium sulfate, and concentrated on a rotovap at ≤50° C. to 20 mL volume.
12. The resulting slurry was diluted with 20 mL of methanol and stirred at RT for 2 h resulting in solids.
13. The solids were collected by filtration, rinsed 2× with 20 mL of refrigerated cold methanol followed by 20 mL of cold heptane.
14. Dried in vacuum oven to constant weight.
15. Weight of crude ST-603 brown pasty powder was 764 mg. TLC showed some product but also many less concentrated side products. Labelled as ST-603-028. GC purity=68%.

Example 33—Synthesis of crude 4-methyl-5-(pyrazin-2-yl)-3H-1,2-dithiole-3-thione, ST-617 (Step 3)

Aim: Carry out Step 3 in toluene and water under reflux using an ammonium salt as a phase transfer catalyst
Procedure
1. Added 5.65 g (0.025 mole) of $P_2S_5$ and 50 mL toluene+5 mL water into a 100-mL 2-neck RBF under nitrogen.
2. Yellow slurry but easily stirrable.
3. Added 100 mg of Aliquat 336 (N-methyl-N,N,N-trioctan-1-ammonium chloride).
4. Heated to 100° C. while stirring.
5. Added crude ST-602-025d solution (12.4 g solution in toluene). Yellow slurry.
6. Started stirring and heated to reflux (~110° C.). Color changed to reddish brown in 15 mins. Fast $H_2S$ gas evolution was observed; gas was passed through a caustic bubbler and no $H_2S$ was exited.
7. Continued reflux for 2 hours.
8. A sample was taken for TLC. No starting material present. Product ST-603 was present but also many other small peaks.
9. The reaction was cooled to 25° C.
10. In a 100-ml beaker was prepared a quenching mixture of 7 g of solid $Na_2CO_3$ dissolved in 30 mL water and 10 mL of THF at RT.
11. To the above beaker was slowly added (over 10 min) the contents of the reaction flask. A weak exotherm was observed but no $H_2S$ gas was detected.
12. The resulting mixture was stirred over 3 hours to complete quench of the reaction (in a very high vent hood attached to a scrubber for safety). Very few insolubles were visible at the end of the 3 hours.
13. The reaction slurry was passed through a 1" celite bed to remove the fine insolubles. Slow filtration.
14. The organic layer was separated (both are colored red), dried over 2 g anhydrous sodium sulfate, and concentrated on a rotovap at ≤50° C. to 20 mL volume.
15. The resulting slurry was diluted with 20 mL of methanol and stirred at RT for 2 h resulting in sticky solids only—no clean powder resulted, so reaction was discarded.

Example 34—Synthesis of crude 4-methyl-5-(pyrazin-2-yl)-3H-1,2-dithiole-3-thione, ST-617 (Step 3)

Aim: Carry out Step 3 in toluene and water under reflux using an ammonium salt as a phase transfer catalyst
Procedure
1. Added 5.65 g (0.025 mole) of $P_2S_5$ and 50 mL toluene+5 mL water into a 100-mL 2-neck RBF under nitrogen.
2. Yellow slurry but easily stirrable.
3. Added 100 mg of benzalkonium chloride.
4. Heated to 100° C. while stirring.
5. Added crude ST-602-025e solution (12.4 g solution in toluene). Yellow slurry.
6. Started stirring and heated to reflux (~110° C.). Color changed to dark brown in 5 mins. Very fast $H_2S$ gas evolution was observed; the gas was passed through a caustic bubbler and no $H_2S$ was exited.
7. Continued reflux for 2 hours.
8. A sample was taken for TLC. No starting material present. Very little product ST-603 was present and lots of streaking was visible on the TLC.
9. With the TLC showing poor conversion the reaction was discarded.

Example 35—Synthesis of crude 4-methyl-5-(pyrazin-2-yl)-3H-1,2-dithiole-3-thione, ST-617 (Step 3)

Aim: Carry out Step 3 in toluene and water under reflux using an ammonium salt as a phase transfer catalyst
Procedure
1. Added 5.65 g (0.025 mole) of $P_2S_5$ and 50 mL toluene+5 mL water into a 100-mL 2-neck RBF under nitrogen.
2. Yellow slurry but easily stirrable.
3. Added 100 mg of benzyltrimethylammonium tribromide.
4. Heated to 100° C. while stirring.
5. Added crude ST-602-025f solution (12.4 g solution in toluene). Brown slurry.
6. Started stirring and heated to reflux (~110° C.). Color changes to brown in 15 min. Moderate $H_2S$ gas evolution was observed; the gas was passed through a caustic bubbler and no $H_2S$ was exited.
7. Continued reflux for 2 hours.
8. A sample was taken for TLC. No starting material present. Product ST-603 was present but also many other compounds in lower concentrations.
9. The reaction was cooled to 25° C.
10. In a 100-mL beaker was prepared a quenching mixture of 7 g of solid $Na_2CO_3$ dissolved in 30 mL water and 10 mL of THF at RT.
11. To the above beaker was slowly added (over 10 min) the contents of the reaction flask. A weak exotherm was observed but no H2s gas was detected.

12. The resulting mixture was stirred over 3 hours to complete quench of the reaction (in a very high vent hood attached to a scrubber for safety). Very few insolubles were visible at the end of the 3 hours.
13. The reaction slurry was passed through a 1" celite bed to remove the fine insolubles. Slow filtration.
14. The organic layer was separated (both are colored red), dried over 2 g anhydrous sodium sulfate, and concentrated on a rotovap at ≤50° C. to 20 mL volume.
15. The resulting slurry was diluted with 20 mL of methanol and stirred at RT for 2 h resulting in sticky solids only.
16. Titurated the sticky solids with a mixture of DMSO+water until brown/red solid powder was formed on the side of the beaker.
17. Collected the solids and checked by TLC. ST-603 was present but still many other trailing spots.
18. Reaction was discarded.

Example 36—Synthesis of crude 4-methyl-5-(pyrazin-2-yl)-3H-1,2-dithiole-3-thione, ST-617 (Step 3)

Aim: Carry out Step 3 in toluene and water under reflux using an ammonium salt as a phase transfer catalyst
Procedure
1. Added 5.65 g (0.025 mole) of $P_2S_5$ and 50 mL toluene+5 mL water into a 100-mL 2-neck RBF under nitrogen.
2. Yellow slurry but easily stirrable.
3. Added 100 mg of tributylammonium acetate.
4. Heated to 100° C. while stirring.
5. Added crude ST-602-025 g solution (12.4 g solution in toluene). Greenish slurry.
6. Started stirring and heated to reflux (~110° C.). Color changed to greenish red-brown in 10 min. Some $H_2S$ gas evolution was observed; the gas was passed through a caustic bubbler and no $H_2S$ was exited.
7. Continued reflux for 2 hours.
8. A sample was taken for TLC. Starting material present. Product ST-603 was also present but a large streak was visible at bottom of TLC.
9. Refluxed for 2 more hours.
10. A sample was taken for TLC. No more starting material present. Product ST-603 was present with a small streak at bottom of TLC
11. The reaction was cooled to 25° C.
12. In a 100-mL beaker was prepared a quenching mixture of 7 g of solid $Na_2CO_3$ dissolved in 30 mL water and 10 mL of THF at RT.
13. To the above beaker was slowly added (over 10 min) the contents of the reaction flask. A weak exotherm was observed but no $H_2S$ gas was detected.
14. The resulting mixture was stirred over 3 hours to complete quench of the reaction (in a very high vent hood attached to a scrubber for safety). Very few insolubles were visible at the end of the 3 hours.
15. The reaction slurry was passed through a 1" celite bed to remove the fine insolubles. VERY slow filtration.
16. The organic layer was separated (both are colored red), dried over 2 g anhydrous sodium sulfate, and concentrated on a rotovap at ≤50° C. to 20 mL volume.
17. The resulting slurry was diluted with 20 mL of methanol and stirred at RT for 2 h resulting in sticky solids only—no clean powder resulted, so reaction was discarded.

Example 37—Synthesis of crude 4-methyl-5-(pyrazin-2-yl)-3H-1,2-dithiole-3-thione, ST-617 (Step 3)

Aim: Carry out Step 3 in toluene and water under reflux using an ammonium salt as a phase transfer catalyst
Procedure
1. Added 5.65 g (0.025 mole) of $P_2S_5$ and 50 mL toluene+5 mL water into a 100-mL 2-neck RBF under nitrogen.
2. Yellow slurry but easily stirrable.
3. Added 100 mg of tetraethylammonium iodide.
4. Heated to 100° C. while stirring.
5. Added crude ST-602-025h solution (12.4 g solution in toluene). Brown slurry.
6. Started stirring and heated to reflux (~110° C.). No color change after 20 mins. No $H_2S$ gas evolution was observed. Regardless, a caustic bubbler was used and no $H_2S$ was exited.
7. Continued reflux for 2 hours.
8. A sample was taken for TLC. Mostly starting material present.
9. Refluxed for 2 more hours.
10. A sample was taken for TLC. Still mostly starting material present. Faint ST-603 spot was present with streaking at bottom of TLC.
11. Refluxed overnight.
12. TLC showed little starting material remaining, but still only a faint ST-603 spot. 13. Reaction was discarded.

Example 38—Synthesis of methyl 2-methyl-3-oxo-3-(pyrazin-2-yl)propanoate, ST-602 (Step 2)

Aim: Scale-up Step 2
Procedure
1. Add 32.8 g (0.2896 mole) of potassium t-butoxide powder and 160 mL of dry THF+40 mL 1,4-dioxane into a 500-mL 2-neck RBF at 0° C. Stirred for 5 minutes.
2. Added 23.2 g (0.2608 mole) of methyl propionate into the flask using a dropping funnel over 15 minutes. Color turned pale yellow.
3. Stirred for an additional 15 minutes at 0° C. No color change.
4. Add 20 g (0.1448 mole) of ST-601 was dissolved in 40 mL of THF+40 mL of 1,4-dioxane and added into the reaction over 30 minutes while allowing the reaction to come to RT (~½ hr). No gas evolution or exotherm.
5. Stirred at RT for 12 hours. Monitored by TLC every 2 hours.
6. 240 mL of distilled water and 240 mL of saturated sodium chloride solution were added to the reaction solution and stirred for 30 minutes.
7. The reaction solution was concentrated to a volume of 510 mL (vacuum of 14 mmHg was adequate on rotovap) and then extracted with 2×240 mL of toluene.
8. The resultant extract was rotovaped to give 97.7 g crude ST-602 as a brown oil with no tarry nature.
9. Divided the solution into eight equal parts and labelled as ST-602-34a, b, c, d, e, f, g, h for comparative cyclization experiments.

Example 39—Synthesis of crude 4-methyl-5-(pyrazin-2-yl)-3H-1,2-dithiole-3-thione, ST-617
(Step 3)

Aim: Carry out Step 3 in toluene and water under reflux using a phosphonium salt as a phase transfer catalyst Procedure
1. Added 5.65 g (0.025 mole) of $P_2S_5$ and 50 mL toluene+5 mL water into a 100-mL 2-neck RBF under nitrogen.
2. Yellow slurry but easily stirrable.
3. Added 100 mg of tetrabutyl phosphonium chloride.
4. Heated to 100° C. while stirring.
5. Added crude ST-602-034a solution (12 g solution in toluene). Yellow-green slurry.
6. Started stirring and heated to reflux (~110° C.). Color changed to red-brown after 20 min. Some $H_2S$ gas evolution was observed; gas was passed through a caustic bubbler and no $H_2S$ was exited.
7. Continued reflux for 2 hours.
8. A sample was taken for TLC. ~50% starting material present. Product ST-603 was also present, in addition to some side products.
9. Continued reflux for 2 hours.
10. A sample was taken for TLC. <5% starting material present. Product ST-603 was present, in addition to some side products.
11. The reaction was cooled to 25° C.
12. In a 100-mL beaker was prepared a quenching mixture of 7 g of solid $Na_2CO_3$ dissolved in 30 mL water and 10 mL of THF at RT.
13. To the above beaker was slowly added (over 10 min) the contents of the reaction flask. No exotherm was observed and no $H_2S$ gas was detected.
14. The resulting mixture was stirred for 2 hours to complete quench of the reaction (in a very high vent hood attached to a scrubber for safety). Some insolubles were visible at the end of the 2 hours.
15. The reaction slurry was passed through a 1" celite bed to remove the fine insolubles. Slow filtration.
16. The organic layer was separated (both are colored red-brown), dried over 2 g anhydrous sodium sulfate, and concentrated on a rotovap at ≤50° C. to 20 mL volume.
17. The resulting slurry was diluted with 20 mL of methanol and stirred at RT for 2 h resulting in sticky solids, but titutration with hexane yielded approximately 400 mg of flowable red-brown powder. TLC showed mostly ST-603—sample saved as ST-603-35.

Example 40—Synthesis of crude 4-methyl-5-(pyrazin-2-yl)-3H-1,2-dithiole-3-thione, ST-617
(Step 3)

Aim: Carry out Step 3 in toluene and water under reflux using a phosphonium salt as a phase transfer catalyst Procedure
1. Added 5.65 g (0.025 mole) of $P_2S_5$ and 50 mL toluene+5 mL water into a 100-mL 2-neck RBF under nitrogen.
2. Yellow slurry but easily stirrable.
3. Added 100 mg of methyltriphenoxyphosphonium iodide.
4. Heated to 100° C. while stirring.
5. Added crude ST-602-034b solution (12 g solution in toluene). Yellow slurry.
6. Started stirring and heated to reflux (~110° C.). Color changed to brown in 1 min. Some $H_2S$ gas evolution was observed; gas was passed through a caustic bubbler and no $H_2S$ was exited.
7. Continued reflux for 2 hours.
8. A sample was taken for TLC. No starting material present. Product ST-603 was present but a large number of other compound also present.
9. The reaction was cooled to 25° C.
10. In a 100-mL beaker was prepared a quenching mixture of 7 g of solid $Na_2CO_3$ dissolved in 30 mL water and 10 mL of THF at RT.
11. To the above beaker was slowly added (over 10 min) the contents of the reaction flask. No exotherm was observed and no $H_2S$ gas was detected.
12. The resulting mixture was stirred for 2 hours to complete quench of the reaction (in a very high vent hood attached to a scrubber for safety). Some insolubles were visible at the end of the 2 hours.
13. The reaction slurry was passed through a 1" celite bed to remove the fine insolubles. Slow filtration.
14. The organic layer was separated (both are colored red-brown), dried over 2 g anhydrous sodium sulfate, and concentrated on a rotovap at ≤50° C. to 20 mL volume.
15. The resulting slurry was diluted with 20 ml of methanol and stirred at RT for 2 h resulting in sticky solids—no clean powder resulted so reaction was discarded.

Example 41—Synthesis of crude 4-methyl-5-(pyrazin-2-yl)-3H-1,2-dithiole-3-thione, ST-617
(Step 3)

Aim: Carry out Step 3 in toluene and water under reflux using a phosphonium salt as a phase transfer catalyst Procedure
1. Added 5.65 g (0.025 mole) of $P_2S_5$ and 50 mL toluene+5 mL water into a 100-ml 2-neck RBF under nitrogen.
2. Yellow slurry but easily stirrable.
3. Added 100 mg of tetraphenyl phosphonium chloride.
4. Heated to 100° C. while stirring.
5. Added crude ST-602-034c solution (12 g solution in toluene). Yellow-green slurry.
6. Started stirring and heated to reflux (~110° C.). Color changed to red-brown after 5 min. Some $H_2S$ gas evolution was observed; gas was passed through a caustic bubbler and no $H_2S$ was exited.
7. Continued reflux for 2 hours.
8. A sample was taken for TLC. ~10% starting material present. Product ST-603 was present, in addition to a number of side products.
9. The reaction was cooled to 25° C.
10. In a 100-mL beaker was prepared a quenching mixture of 7 g of solid $Na_2CO_3$ dissolved in 30 mL water and 10 mL of THF at RT.
11. To the above beaker was slowly added (over 10 min) the contents of the reaction flask. No exotherm was observed and no $H_2S$ gas was detected.
12. The resulting mixture was stirred for 2 hours to complete quench of the reaction (in a very high vent hood attached to a scrubber for safety). Some insolubles were visible at the end of the 2 hours.
13. The reaction slurry was passed through a 1" celite bed to remove the fine insolubles. Slow filtration.

14. The organic layer was separated (both are colored red-brown), dried over 2 g anhydrous sodium sulfate, and concentrated on a rotovap at ≤50° C. to 20 mL volume.
15. The resulting slurry was diluted with 20 ml of methanol and stirred at RT for 2 h resulting in sticky solids. Titration did not yield any flowable powder product—so, reaction was discarded.

Example 42—Synthesis of crude 4-methyl-5-(pyrazin-2-yl)-3H-1,2-dithiole-3-thione, ST-617 (Step 3)

Aim: Carry out Step 3 in toluene and water under reflux using a phosphonium salt as a phase transfer catalyst
Procedure
1. Added 5.65 g (0.025 mole) of $P_2S_5$ and 50 mL toluene+5 mL water into a 100-mL 2-neck RBF under nitrogen.
2. Yellow slurry but easily stirrable.
3. Added 100 mg of trihexyltetradecylphosphonium chloride.
4. Heated to 100° C. while stirring
5. Added crude ST-602-034d solution (12 g solution in toluene). Brown slurry.
6. Started stirring and heated to reflux (~110° C.). No color change after 20 mins. Some $H_2S$ gas evolution was observed; gas was passed through a caustic bubbler and no $H_2S$ was exited.
7. Continued reflux for 2 hours.
8. A sample was taken for TLC. No starting material present. Very little product spot if at all and many side products detected—so, reaction was discarded without work up.

Example 43—Synthesis of crude 4-methyl-5-(pyrazin-2-yl)-3H-1,2-dithiole-3-thione, ST-617 (Step 3)

Aim: Carry out Step 3 in toluene under reflux using an ammonium salt as a phase transfer catalyst
Procedure
1. Added 5.65 g (0.025 mole) of $P_2S_5$ and 50 mL toluene into a 100-ml 2 neck RBF under nitrogen.
2. Yellow slurry but easily stirrable.
3. Added 200 mg of Aliquat HTA-1.
4. Heated to 100° C. while stirring.
5. Added crude ST-602-034e solution (12 g solution in toluene). Yellow slurry.
6. Started stirring and heated to reflux (~110° C.). Color changed to red-brown after 10 min. Some $H_2S$ gas evolution was observed; gas was passed through a caustic bubbler and no $H_2S$ was exited.
7. Continued reflux for 2 hours.
8. A sample was taken for TLC. <10% starting material present. Product ST-603 was present but few other spots also present.
9. Continued reflux for 2 hours.
10. A sample was taken for TLC. <5% starting material present. Product ST-603 was present but some other spots also present.
11. The reaction was cooled to 25° C.
12. In a 100-mL beaker was prepared a quenching mixture of 7 g of solid $Na_2CO_3$ dissolved in 30 mL water and 10 mL of THF at RT.
13. To the above beaker was slowly added (over 10 min) the contents of the reaction flask. Mild exotherm was observed but no $H_2S$ gas was detected.
14. The resulting mixture was stirred for 2 hours to complete quench of the reaction (in a very high vent hood attached to a scrubber for safety). Some insolubles were visible at the end of the 2 hours.
15. The reaction slurry was passed through a 1" celite bed to remove the fine insolubles. Slow filtration.
16. The organic layer was separated (both are colored red-brown), dried over 2 g anhydrous sodium sulfate, and concentrated on a rotovap at ≤50° C. to 20 mL volume.
17. The resulting slurry was diluted with 20 mL of methanol and stirred at RT for 2 h resulting in slighty sticky solids. Titutration with hexane yielded 830 mg of flowable red-brown powder. TLC showed mostly ST-603—sample saved as ST-603-39.

INCORPORATION BY REFERENCE

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents, and published patent applications, and patent applications cited throughout this application are incorporated herein by reference.

I claim:
1. A method of making a composition comprising oltipraz, comprising the steps of:
   (i) reacting a quantity of pyrazine-2-carboxylic acid methyl ester with methyl propionate to form methyl 2-methyl-3-oxo-3-(pyrazin-2-yl)propanoate, wherein the reaction is carried out in the presence of a base comprising potassium t-butoxide or sodium pentanoate, and a solvent comprising 1,4-dioxane in tetrahydrofuran (THF), wherein the ratio of 1,4-dioxane in the THF is at least about 1:5;
   (ii) adding at least one aqueous liquid to quench the reaction in Step (i);
   (iii) adding a nonpolar organic solvent and an ionic salt, thereby forming a composition comprising an aqueous component and an organic component, wherein the organic component comprises the nonpolar solvent and methyl 2-methyl-3-oxo-3-(pyrazin-2-yl) propanoate;
   (iv) separating the organic component from the aqueous component;
   (v) reacting the methyl 2-methyl-3-oxo-3-(pyrazin-2-yl) propanoate ester in the organic component with $P_2S_5$ in the presence of a nonpolar organic solvent to form 4-methyl-5-(pyrazin-2-yl)-3H-1,2-dithiole-3-thione (oltipraz).
2. A method according to claim 1, wherein the ratio of 1,4-dioxane to THF in Step (i) is from about 1:5 to about 1:3.

3. A method according to claim 2, wherein, the ratio of 1,4-dioxane to THF is about 1:4.

4. A method according to claim 1, wherein the base comprises potassium t-butoxide.

5. A method according to claim 1, wherein the mole ratio of the base to methyl propionate is from about 3:1 to about 1:1.

6. A method according to claim 1, wherein the nonpolar organic solvent used in Step (iii) comprises toluene.

7. A method according to claim 1, wherein the nonpolar organic solvent in Step (v) comprises toluene.

8. A method according to claim 1, wherein the nonpolar solvent in Step (iii) is the same nonpolar solvent used in Step (v).

9. A method according to claim 1, wherein the yield of oltipraz is greater than 21% based on the amount of pyrazine-2-carboxylic acid methyl ester.

* * * * *